(12) United States Patent
Mackinnon et al.

(10) Patent No.: US 11,579,152 B2
(45) Date of Patent: Feb. 14, 2023

(54) ENGINEERED HERG CHANNEL PROTEINS, VESICLES AND METHODS OF IDENTIFYING SMALL MOLECULE PHARMACOLOGICAL AGENTS

(71) Applicant: The Rockefeller University, New York, NY (US)

(72) Inventors: Roderick Mackinnon, New York, NY (US); Zhenwei Su, New York, NY (US); Weiwei Wang, NY, NY (US)

(73) Assignee: The Rockefeller University, New York, NY (US)

( * ) Notice: Subject to any disclaimer, the term of this patent is extended or adjusted under 35 U.S.C. 154(b) by 534 days.

(21) Appl. No.: 16/086,676

(22) PCT Filed: Mar. 31, 2017

(86) PCT No.: PCT/US2017/025356
§ 371 (c)(1),
(2) Date: Sep. 20, 2018

(87) PCT Pub. No.: WO2017/173257
PCT Pub. Date: Oct. 5, 2017

(65) Prior Publication Data
US 2021/0102956 A1  Apr. 8, 2021

Related U.S. Application Data

(60) Provisional application No. 62/317,043, filed on Apr. 1, 2016.

(51) Int. Cl.
*G01N 33/68* (2006.01)
*C07K 14/47* (2006.01)
*G01N 21/64* (2006.01)

(52) U.S. Cl.
CPC ......... *G01N 33/6872* (2013.01); *C07K 14/47* (2013.01); *G01N 21/6428* (2013.01); *G01N 2021/6439* (2013.01); *G01N 2500/04* (2013.01); *G01N 2500/10* (2013.01)

(58) Field of Classification Search
CPC ............... A61K 39/00; G01N 21/6428; G01N 33/6872; G01N 2021/6439

USPC .......................................... 424/184.1, 185.1
See application file for complete search history.

(56) References Cited

U.S. PATENT DOCUMENTS

| | | | |
|---|---|---|---|
| 5,986,081 A | 11/1999 | Ganetzky et al. | |
| 6,087,488 A | 7/2000 | Ganetzky et al. | |
| 9,068,280 B2 | 6/2015 | Poulos et al. | |
| 2001/0034024 A1* | 10/2001 | Keating | C12Q 1/6883 435/6.17 |
| 2006/0183166 A1 | 8/2006 | Mayer et al. | |
| 2007/0225227 A1 | 9/2007 | Doranz | |

OTHER PUBLICATIONS

Vandenberg et al., 2012, Physiol. Rev 92: 1393-1478 (Year: 2012).*
Thomas, D. et al., Deletion of Protein Kinase A Phosphorylation Sites in the HERG Potassium Channel Inhibits Activation Shift by Protein Kinase A, Journal of Biological Chemistry, Sep. 24, 1999, vol. 274, No. 39; pp. 27457-27462; p. 27458, 2nd column, 2nd paragraph; DOI: 10.1074/jbc.274.39.27457.
Zhang, Y. et al. hERG ion channel pharmacology: cell membrane liposomes in porous-supported lipid bilayers compared with whole-cell patch-clamping. European Biophysical Journal, Nov. 2012, vol. 41, No. 11, pp. 949-958; p. 949, 2nd column 1st paragraph; p. 950, 2nd column 2nd paragraph; DOI: 10.1007/s00249-012-0852-2.
Friddin, M.S. et al., Single-channel electrophysiology of cell-free expressed ion channels by direct incorporation in lipid bilayers, Analyst, Nov. 12, 2013, vol. 138, No. 24; pp. 7294-7298; abstract; p. 7294, 1st column, 1st paragraph; p. 7296, 2nd column, 3rd paragraph; SI information, p. 1, 1st paragraph; DOI: 10.1039/c3an01540h.
Su, Z. et al., Novel cell-free high-throughput screening method for pharmacological tools targeting K+ channels, Proceedings of the National Academy of Sciences of the U.S.A., May 17, 2016, vol. 113, No. 20; pp. 5748-5753; DOI: 10.1073/pnas.1602815113.

* cited by examiner

*Primary Examiner* — Robert S Landsman
(74) *Attorney, Agent, or Firm* — Hoffmann & Baron, LLP

(57) ABSTRACT

The present invention provides methods and compositions relating to an assay for hERG channel protein sensitivity to small molecule pharmacological agents. In one embodiment, the invention includes an engineered hERG channel protein. In another embodiment, the invention includes a method of identifying small molecule pharmacological agents that interfere with repolarization of cardiac cells.

17 Claims, 26 Drawing Sheets

Specification includes a Sequence Listing.

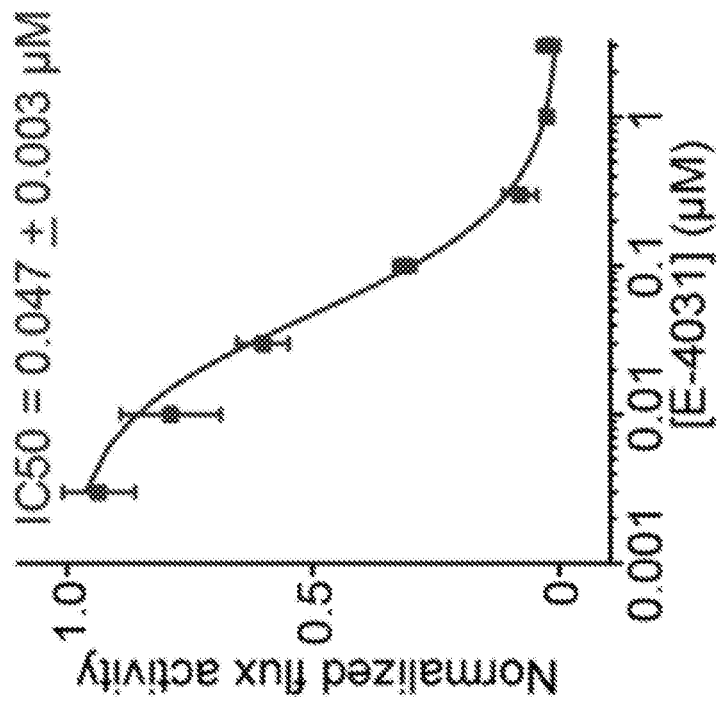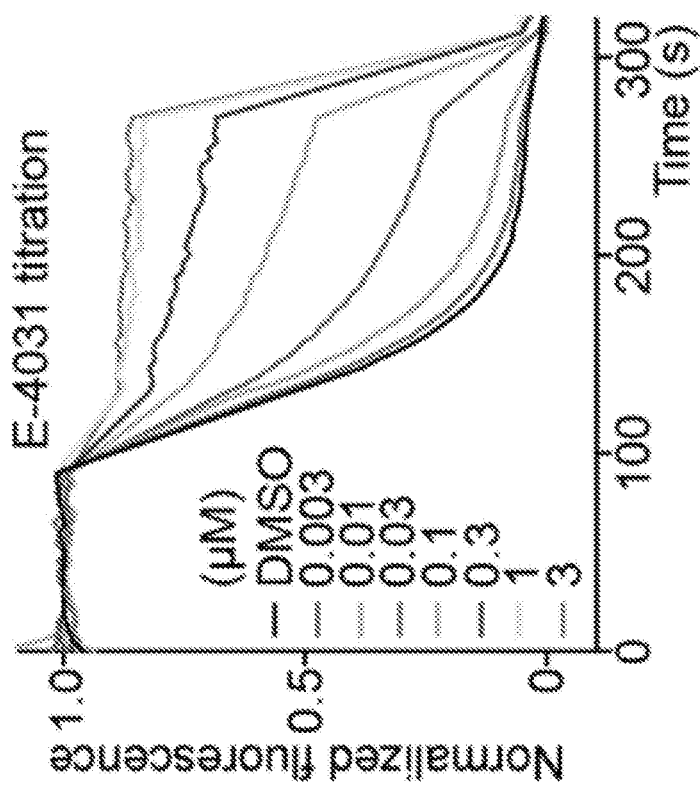
Figure 3A

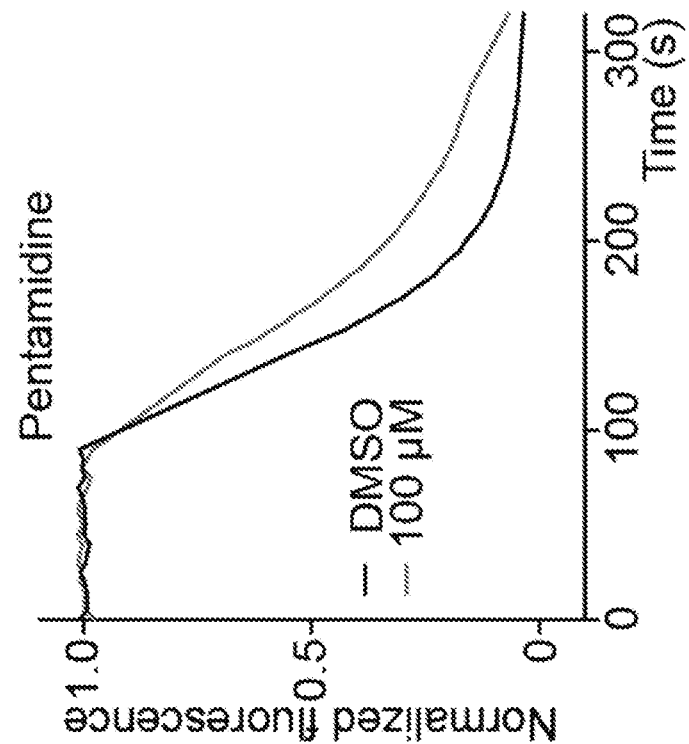
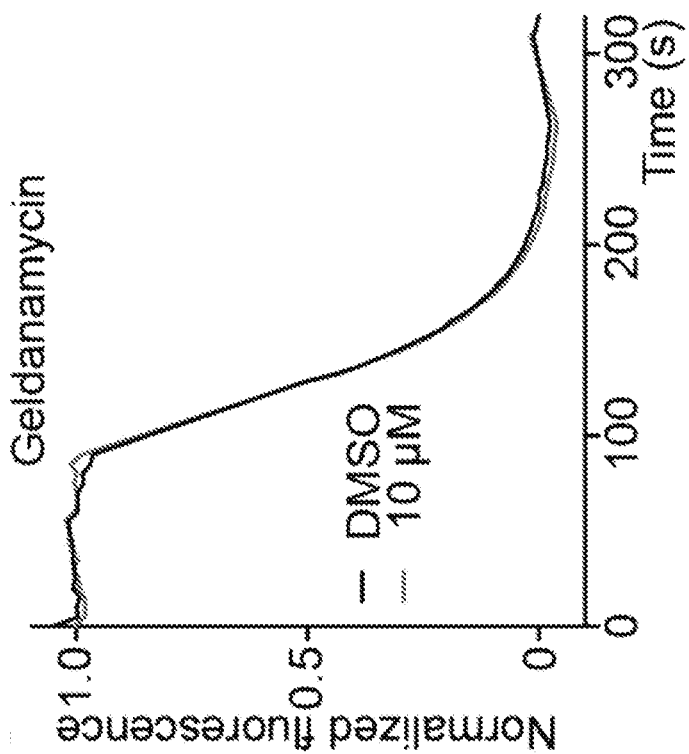
Figure 4E
Figure 4F

```
hERG_AAE37063.1/1-1159      1 MPVRGHVAPQNTFLDTIIRKFEGQSRKFIIANARVENCAVTYCNDGFCELCGYSRAEVMQRPCTCDFLHGPRTQRRAAAQIAQLLGAEERKVEIAFYRKDGSCFLCLVDVVP 114
hERG_Q12809.1/1-1159        1 MAVRRGHVAPQNTFLDTIIRKFEGQSRKFIIANARVENCAVTYCNDGFCELCGYSRAEVMQRPCTCDFLHGPRTQRRAAAQIAQLLGAEERKVEIAFYRKDGSCFLCLVDVVP 114
hERG_mutant/1-784           1 MAVRRGHVAPQNTFLDTIIRKFEGQSRKFIIANARVENCAVTYCNDGFCELCGYSRAEVMQRPCTCDFLHGPRTQRRAAAQIAQLLGAEERKVEIAFYRKDGSCFLCLVDVVP 114 hERG_AAE37063.1/1-1159    114 VKNEDGAVIMFIILNFEVVMEKDMVGSPAHDTNHRGPPTSWLAPGRAKTFRLKLPALLALTARESSVRSGGAGGAGAPGAVVVDVDLTPAAPSSESLALDEVTAMDNHVAGLGPA 228
hERG_Q12809.1/1-1159      114 VKNEDGAVIMFIILNFEVVMEKDMVGSPAHDTNHRGPPTSWLAPGRAKTFRLKLPALLALTARESSVRSGGAGGAGAPGAVVVDVDLTPAAPSSESLALDEVTAMDNHVAGLGPA 228
hERG_mutant/1-784         114 VKNEDGAVIMFIILNFEVVMEKDMVGS--------------------------------------------------------------------------------------- 140 hERG_AAE37063.1/1-1159    229 EERRALVGPGSPPRSAPGQLPSPRAHSLNPDASGSSCSLARTRSRESCASVRRASSADDIEAMRAGVLPPPRHASTGAMPLRSGLLNSTSDSDLVRYRTISKIPQITLNFVD 342
hERG_Q12809.1/1-1159      229 EERRALVGPGSPPRSAPGQLPSPRAHSLNPDASGSSCSLARTRSRESCASVRRASSADDIEAMRAGVLPPPRHASTGAMPLRSGLLNSTSDSDLVRYRTISKIPQITLNFVD 342
hERG_mutant/1-784             -------------------------------------------------------------------------------------------------------------- hERG_AAE37063.1/1-1159    343 LKGDPFLASPTSDREIIAPKIKERTHNVTEKVTQVLSLGADVLPEYKLQAPRIHRWTILHYSPFKAVWDWLILLLVIYTAVFTPYSAAFLLKETEEGPPATECGYACQPLAVVD 456
hERG_Q12809.1/1-1159      343 LKGDPFLASPTSDREIIAPKIKERTHNVTEKVTQVLSLGADVLPEYKLQAPRIHRWTILHYSPFKAVWDWLILLLVIYTAVFTPYSAAFLLKETEEGPPATECGYACQPLAVVD 456
hERG_mutant/1-784         141 --------------GADVLPEYKLQAPRIHRWTILHYSPFKAVWDWLILLLVIYTAVFTPYSAAFLLKETEEGPPATECGYACQPLAVVD 216 hERG_AAE37063.1/1-1159    457 LIVDIMFIVDILINFRTTYVNANEEVVSHPGRIAVHYFKGWFLIDMVAAIPFDLLIFGSGEELIGLLKTARLLRLVRVARKLDRYSEYGAAVLFLLMCTFALIAHWLACIWYA 570
hERG_Q12809.1/1-1159      457 LIVDIMFIVDILINFRTTYVNANEEVVSHPGRIAVHYFKGWFLIDMVAAIPFDLLIFGSGEELIGLLKTARLLRLVRVARKLDRYSEYGAAVLFLLMCTFALIAHWLACIWYA 570
hERG_mutant/1-784         217 LIVDIMFIVDILINFRTTYVNANEEVVSHPGRIAVHYFKGWFLIDMVAAIPFDLLIFGSGEELIGLLKTARLLRLVRVARKLDRYSEYGAAVLFLLMCTFALIAHWLACIWYA 330 hERG_AAE37063.1/1-1159    571 IGNMEQPHMDSRIGWLHNLGDQIGKPYNSSGLGGPSIKDKYVTALYFTFSSLTSVGFGNVSPNTNSEKIFSICVMLIGSLMYASIFGNVSAIIQRLYSGTARYHTQMLRVREFI 684
hERG_Q12809.1/1-1159      571 IGNMEQPHMDSRIGWLHNLGDQIGKPYNSSGLGGPSIKDKYVTALYFTFSSLTSVGFGNVSPNTNSEKIFSICVMLIGSLMYASIFGNVSAIIQRLYSGTARYHTQMLRVREFI 684
hERG_mutant/1-784         331 IGNMEQPHMDSRIGWLHNLGDQIGKPYNSSGLGGPSIKDKYVTALYFTFSSLTSVGFGNVSPNTNSEKIFSICVMLIGSLMYASIFGNVSAIIQRLYSGTARYHTQMLRVREFI 444 hERG_AAE37063.1/1-1159    685 RFHQIPNPLRQRLEEYFQHAWSYTNGIDMNAVLKGFPECLQADICLHLNRSLLQHCKPFRGATKGCLRALAMKFKTTHAPPGDTLVHAGDLLTALYFISRGSIELLRGDVVVAI 798
hERG_Q12809.1/1-1159      685 RFHQIPNPLRQRLEEYFQHAWSYTNGIDMNAVLKGFPECLQADICLHLNRSLLQHCKPFRGATKGCLRALAMKFKTTHAPPGDTLVHAGDLLTALYFISRGSIELLRGDVVVAI 798
hERG_mutant/1-784         445 RFHQIPNPLRQRLEEYFQHAWSYTNGIDMNAVLKGFPECLQADICLHLNRSLLQHCKPFRGATKGCLRALAMKFKTTHAPPGDTLVHAGDLLTALYFISRGSIELLRGDVVVAI 558 hERG_AAE37063.1/1-1159    799 LGKNDIFGEPLNLYARPGKSNGDVRALTYCDLLEKIHRDDLLEVLDMYPEFSDHFWSSLEITFNLRDTNMIPGSPGSTELEGGFSRQRKRKLSFRRRTDKDTEQPGEVSALGPGR 912
hERG_Q12809.1/1-1159      799 LGKNDIFGEPLNLYARPGKSNGDVRALTYCDLLEKIHRDDLLEVLDMYPEFSDHFWSSLEITFNLRDTNMIPGSPGSTELEGGFSRQRKRKLSFRRRTDKDTEQPGEVSALGPGR 912
hERG_mutant/1-784         559 LGKNDIFGEPLNLYARPGKSNGDVRALTYCDLLEKIHRDDLLEVLDMYPEFSDHFWSSLEITFNLRDTNMIPG------------------------------------------ 630 hERG_AAE37063.1/1-1159    913 AGAGPSSRGRPGGPWGESPSSGPSSPESSEDEGPGRSSSPLRLVPFSSPRPPGGEPPGGEPLMEDCEKSSDTCNPLSGAFSGVSNIFSFWGDSRGRQYQELPRCPAFTPSLLNIP 1026
hERG_Q12809.1/1-1159      913 AGAGPSSRGRPGGPWGESPSSGPSSPESSEDEGPGRSSSPLRLVPFSSPRPPGGEPPGGEPLMEDCEKSSDTCNPLSGAFSGVSNIFSFWGDSRGRQYQELPRCPAFTPSLLNIP 1026
hERG_mutant/1-784         631 ----------------------------------------------------------------------------------------GRQYQELPRCPAFTPSLLNIP 651 hERG_AAE37063.1/1-1159   1027 LSSPGRRPRGDVESRLDALQRQLNRLETRLSADMATVLQLIQRQMTLVPPAYSAVTTPGPGPTSTSPLLFVSPLPFLTLDSLSQVSQFMACEELPPGAPELPQEGFTRRLSLPG 1140
hERG_Q12809.1/1-1159     1027 LSSPGRRPRGDVESRLDALQRQLNRLETRLSADMATVLQLIQRQMTLVPPAYSAVTTPGPGPTSTSPLLFVSPLPFLTLDSLSQVSQFMACEELPPGAPELPQEGFTRRLSLPG 1140
hERG_mutant/1-784         652 LSSPGRRPRGDVESRLDALQRQLNRLETRLSADMATVLQLIQRQMTLVPPAYSAVTTPGPGPTSTSPLLFVSPLPFLTLDSLSQVSQFMACEELPPGAPELPQEGFTRRLSLPG 765 hERG_AAE37063.1/1-1159   1141 QLGALTSQPLHRHGSDPGS 1159
hERG_Q12809.1/1-1159     1141 QLGALTSQPLHRHGSDPGS 1159
hERG_mutant/1-784         766 QLGALTSQPLHRHGSDPGS 784
```

Figure 6

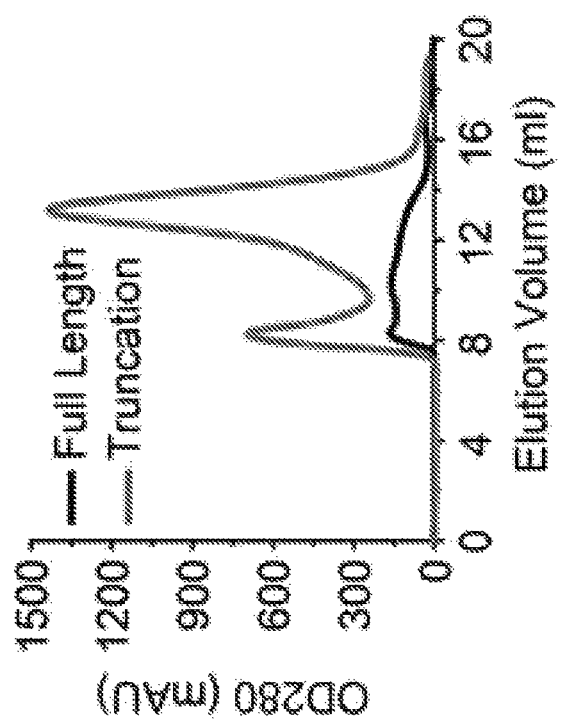
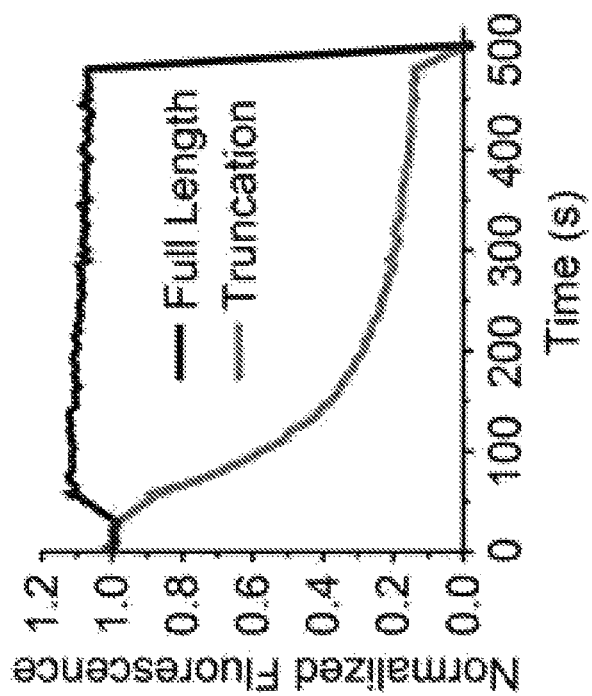
Figure 7A
Figure 7B

ENGINEERED HERG CHANNEL PROTEINS, VESICLES AND METHODS OF IDENTIFYING SMALL MOLECULE PHARMACOLOGICAL AGENTS

CROSS-REFERENCE TO RELATED APPLICATIONS

This application is a national stage filing under 35 USC § 371 of International PCT Application number PCT/US2017/025356, filed Mar. 31, 2017, and claims the benefit of U.S. Provisional Application No. 62/317,043, filed Apr. 1, 2016, all of which are hereby incorporated by reference in their entirety.

STATEMENT OF GOVERNMENT RIGHTS

The present application was made with government support under project number 5R01GM043949 awarded by the National Institutes of Health (NIH). The United States government has certain rights in the invention(s).

BACKGROUND

The $K^+$ channel superfamily can be divided into 5 subfamilies, including $K_{ir}$ (inwardly-rectifying $K^+$ channels), K2P (tandem-pore-domain $K^+$ channels), $K_v$1-9 (voltage-gated $K^+$ channels), $K_v$10-12 (including the hERG channel), and $K_{Ca}$ ($Ca^{2+}$-activated $K^+$ channels)[1,2] (FIG. 1A). Their varied structures and gating mechanisms reflect their diverse and important roles in biology.

$K_{ir}$ and K2P channels are major regulators of the resting membrane potential. Among $K_{ir}$ channels, $K_{ir}$3.2 (G-protein-activated inwardly-rectifying $K^+$ channel member 2, GIRK2) regulates the electrical excitability of many different neurons in response to inhibitory G protein coupled receptor (GPCR) stimulation[3]. $K_{ir}$6.2 (K-ATP) controls insulin secretion in beta cells and is a well-established drug target for diabetes[3].

The biological functions of K2P channels remain mostly unknown due to the lack of pharmacological tools. For example, TRAAK (TWIK (Tandom pore domain in a Weak Inwardly rectifying $K^+$ channel) Related Arachidonic Acid stimulated $K^+$ channel) is biophysically mechanosensitive, but little is known about its biology, especially regarding its mechanosensitivity[4-7]. $K_v$ channels repolarize action potentials. Mutations in Kv7.1 (KCNQ1) cause congenital long QT syndrome[2]. The human Ether-a-go-go-Related Gene (hERG) (Kv11.1) channel is the dangerous off-target of many drugs that, by inadvertently inhibiting hERG, cause drug-induced long QT syndrome with the potential of torsades de pointes and sudden death[8]. High-conductance $Ca^{2+}$-activated $K^+$(Slo1) channels of the $K_{Ca}$ subfamily regulate smooth muscle contraction, and activators of the Slo1 channel are drug candidates for asthma, over-reactive bladder, and hypertension[9-15]. These are just a small subset of examples illustrating the important roles of $K^+$ channels to different physiological functions.

The hERG channel is an example of a voltage-gated potassium ion channel. The hERG channel is present in cardiac cells where it participates in repolarization of the action potential. When hERG function is impeded a characteristic lengthening of the Q-T interval is detectable on the electrocardiogram of mammals. This phenomenon is associated in humans with a lethal arrhythmia called torsade de pointes. For a reason that is not well understood, the hERG channel is highly susceptible to blockage by many different small molecule drugs. hERG inhibition is an important antitarget that must be avoided during drug development. The ability to predict which small molecules will block hERG is poor and therefore all drugs in development are tested in a hERG activity assay. None of the methods currently used—electrophysiology[16,17], cell-based $Tl^+$ flux assay/membrane potential dye assay[18,19], binding/inhibitor competition assay[20,21] provide a robust, affordable, and efficient way to evaluate whether small molecule pharmacological agents block or interfere with hERG.

Therefore, there remains a need for a robust, affordable, and efficient way to evaluate small molecule pharmacological agents and their effects on hERG function.

SUMMARY OF THE INVENTION

The present invention provides methods and compositions relating to an assay for hERG channel protein sensitivity to small molecule pharmacological agents.

In one embodiment, the present invention provides an engineered hERG protein comprising SEQ ID NO. 3, or a homolog thereof with at least 90% homology thereto.

In another embodiment, the present invention provides a vesicle comprising: a liposome and a polypeptide comprising SEQ ID NO. 3.

In yet another embodiment, the present invention provides a method of identifying small molecule pharmacological agents that interfere with repolarization of cardiac cells. The method includes: (a) contacting the vesicle described above with a test pharmacological agent, and a lipophilic pH-sensitive fluorescent dye; (b) measuring fluorescence; (c) contacting said vesicle with a proton ionophore to initiate ion flux; (d) measuring pH-sensitive fluorescence of the dye; and (e) identifying the small molecule pharmacological agent as a small molecule pharmacological agent that affects hERG function when the fluorescence level at step (d) is substantially similar to the fluorescence level at step (b).

DESCRIPTION OF THE FIGURES

FIGS. 3A-3G. Characterization of hERG positive control drugs. (3A-3D) Efflux curves and dose response curves of well-characterized hERG blockers, E-4031, ibutilide, pimozide and verapamil (n=3 each). (3E-3G) Efflux curves and dose response curves using drugs that were withdrawn from the market because of risk of serious cardiac arrhythmias and increased risk of sudden death. These drugs have been shown to inhibit hERG activities from electrophysiological recordings. The LFA IC50 values correlate well to electrophysiological recordings with an approximate 10-fold IC50 offset. All data are mean±SEM.

FIGS. 4A-4I. Validation of hERG negative control drugs. (4A-4D) Four widely used drugs, aspirin, HMR1556, ampicillin, and salbutamol, that are known not to inhibit hERG, did not inhibit hERG-mediated efflux in LFA at a concentration of 100 μM (n=3 each). (4E-4I) Five drugs that are reported to inhibit hERG trafficking to plasma membrane were negative in the hERG efflux assay at 10 μM (Geldanamycin) and 100 μM (others), (n=3 each).

FIG. 6. Sequence alignment of hERG wild type proteins AAE37063.1 (SEQ ID NO. 1) and Q128091 (SEQ ID NO. 2) and an engineered hERG channel protein mutant SEQ ID NO. 3.

FIGS. 7A-7B. Comparison of wild-type and truncated hERG. (A) shows a gel filtration chromatogram of both. As you can see, the wild type protein (full length) elutes as aggregated protein whereas truncated protein elutes as a mono disperse peak. This directly demonstrates that the truncation protein is well behaved and the wild type is not. (B) shows the two proteins in LFA. Wild type protein gives no signal whereas truncated protein gives a prominent flux signal.

DETAILED DESCRIPTION

Figure 1A:
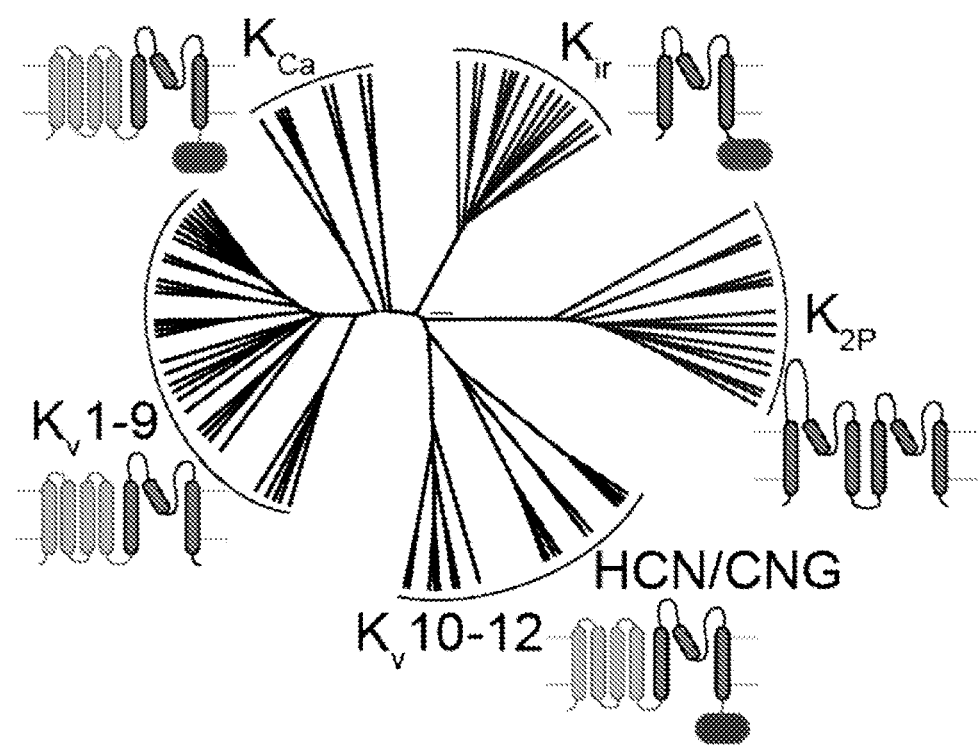
FIGS. 1A-1D. Introduction to the liposome flux assay (LFA). (1A) A phylogenetic tree of human $K^+$ Channels adapted from ref.4. The $K^+$ Channel superfamily can be divided into 5 subfamilies, including $K_{ir}$ (inwardly-rectifying $K^+$ Channels), K2P (tandem-pore-domain $K^+$ Channels), $K_v$1-9 (voltage-gated $K^+$ Channels), $K_v$10-12 (including the hERG channel), and $K_{Ca}$ ($Ca^{2+}$-activated $K^+$Channels). $K_v$10-12 subfamily is related to HCN/CNG channels (hyperpolarization-activated cyclic nucleotide-gated channels/cyclic nucleotide-gated channels). Dark grey highlights the conserved pore domain, light grey highlights the voltage sensor domain, and black highlights the intracellular ligand-binding domain. (1B) A cartoon of the LFA. Purified $K^+$ channels are reconstituted into lipid vesicles in the presence of high KCl. To assay, thawed vesicles are diluted into a high NaCl solution, which creates a strong gradient for the efflux of $K^+$. Potassium efflux is initiated by the addition the $H^+$ ionophore carbonyl cyanide m-chlorophenylhydrazone (CCCP), which allows influx of $H^+$ to counterbalance the efflux of $K^+$. The RE influx is monitored by the $H^+$-dependent quenching of a fluorescent dye, 9-amino-6-chloro-2-methoxyacridine (ACMA). (1C) A representative trace of the LFA. $K^+$ efflux leads to dye quenching when $K^+$ channels are open (light grey trace), but not when they are closed or inhibited (dark grey trace). The $K^+$ ionophore valinomycin is finally added to allow $K^+$ Channel-independent efflux, to exclude false positive compounds with strong auto-fluorescence or causing vesicle lysis. (1D) A cartoon of the cell-free high throughput screening procedure. All flux components were added and mixed automatically by FDSS6000 plate reader in sequence as depicted in the figure. Valinomycin, used to induce channel-independent K⁺ efflux, was not used in the primary screen on FDSS6000 because it was hard to wash out and caused contamination among plates.

The present invention provides compositions and methods for the identification of small molecule pharmacological agents that affect potassium ion channel function. Potassium ion channels include transmembrane proteins that allow the flow of potassium ions across a lipid bilayer.

hERG Channel Protein

The hERG channel protein is one example of a transmembrane protein that forms a potassium ion channel. In one embodiment, the invention provides an engineered hERG channel protein that is, unlike the wild type protein, stable, easy to purify, and amenable to use in a high throughput screening assay.

The hERG channel is an example of a voltage-gated potassium ion channel. The hERG channel is present in cardiac cells where it participates in repolarization of the action potential. When hERG function is impeded a characteristic lengthening of the Q-T interval is detectable on the electrocardiogram of mammals. This phenomenon occurs in people with a lethal arrhythmia called torsade de pointes.

Genbank accession No. AAE37063.1 provides the sequence of a hERG channel protein (1159 residues). It is an example of one isoform of the wild-type sequence of the hERG channel protein encoded by the hERG gene. Uniprot identifier Q12809-1 provides another sequence of a hERG channel protein (1159 residues); it is different from AAE37063.1 by a single mutation, alanine to proline.

The wild type hERG channel protein is unstable and aggregates when purified and thus is unsuitable for high throughput screening based on biochemical purification.

Through extensive analysis, it has been discovered that modification of the hERG channel protein amino acid sequence by deleting amino acid residues within two different intracellular loops yield a biochemically well-behaved hERG channel protein that could be purified with good function and correct pharmacology. In particular, the loops lie within the residue positions 120 and 410 (region 1) and within residue positions 850 and 1070 (region 2) These limits are defined on the basis of our biochemical and structural analysis of the hERG channel[22]. Deletion of amino acids within these residue limits permit expression and purification of the hERG channel protein that provides a protein that is functional and stable, thus making it possible to carry out the high throughput screening method described herein.

In some embodiments, the engineered hERG channel protein includes deletions of more than 25, more than 50, more than 100, more than 200 residues within one or both of region 1 and region 2. In another embodiment, the engineered hERG channel protein includes deletion of the entirety of one or both of region 1 and region 2.

In one embodiment, the engineered hERG channel protein mutant includes internal deletions of one or both of residues 141-380 and 871-1005 and provides a protein that is functional, stable, and easy to work with. This mutant is biochemically very stable but pharmacologically similar to wild-type. In one embodiment, the engineered hERG channel protein of the present invention includes SEQ ID NO. 3. FIG. 6 shows an alignment of SEQ ID NO. 3 with Genbank accession No. AAE37063.1 (SEQ ID NO. 1) and Uniprot identifier Q12809-1 (SEQ ID NO. 2). FIG. 7 compares the gel filtration chromatogram of wild type hERG and an engineered hERG channel protein mutant as disclosed herein, (SEQ ID NO. 3).

Embodiments of the invention also relate to isolated and/or purified polypeptide of SEQ ID NO. 3, or a homologue or fragment thereof. In other embodiments, the invention provides a nucleotide sequence that encodes SEQ ID NO. 3, or a homologue or fragment thereof.

In yet another embodiment, the invention provides a polypeptide that has at least 95% sequence identity to SEQ ID NO. 3. In yet another embodiment, the invention provides a polypeptide that has at least 90% sequence identity to SEQ ID NO. 3. In yet another embodiment, the invention provides a polypeptide that has at least 85% sequence identity to SEQ ID NO. 3. In yet another embodiment, the invention provides a polypeptide that has at least 80% sequence identity to SEQ ID NO. 3.

Vesicle

In one embodiment, the invention provides a vesicle having a lipid bilayer and the engineered hERG channel protein described above, creating a liposome or a proteoliposome.

The term "liposome" as used herein refers to an artificially prepared vesicle composed of a lipid bilayer. The term "lipid bilayer" as used herein refers to a membrane made of two layers of lipid molecules. The lipid bilayer may have a similar thickness as that of a naturally existing bilayer, such as a cell membrane, a nuclear membrane, and a virus envelope. For example, the lipid bilayer may have a thickness of about 10 nm or less, for example, in a range of about 1 nm to about 9 nm, about 2 nm to about 8 nm, about 2 nm to about 6 nm, about 2 nm to about 4 nm, or about 2.5 nm to about 3.5 nm. The lipid bilayer is a barrier that keeps ions, proteins, and other molecules in an area, and/or prevents them from diffusing into other areas. The "lipid molecules" forming the lipid bilayer may be a molecule including a hydrophilic head and hydrophobic tails. The lipid molecule may have 14 to 50 carbon atoms.

The lipid bilayer may be phospholipid, a lipid conjugated to polyethylene glycol (PEG), cholesterol, elastin-like polypeptide, or any combination thereof.

As used herein "phospholipid" refers to a compound lipid containing phosphate ester within a molecule, and is a main component of biological membranes, such as cell membranes, endoplasmic reticulum, mitochondria, and myelin sheath around nerve fibers. The phospholipid includes a hydrophilic head and two hydrophobic tails. When the phospholipids are exposed to water, they arrange themselves into a two-layered sheet (a bilayer) with all of their tails pointing toward the center of the sheet. The center of this bilayer contains almost no water and also excludes molecules such as sugars or salts that dissolve in water but not in oil. The phospholipid may include phosphatidic acid, phosphatidylethanolamine, phosphatidylglycerol, phosphatidylcholine, phosphatidylserine, phosphatidylinositol, phosphosphingolipid, or any combination thereof.

Phosphatidylcholine (PC) may include choline as a head group and glycerophosphoric acid as a tail, wherein glycerophosphoric acid may be saturated fatty acid or unsaturated fatty acid and have 14 to 50 carbon atoms. Examples of the PC include 1,2-dipalmitoyl-sn-glycero-3-phosphocholine (DPPC), 1,2-distearoyl-sn-glycero-3-phosphocholine (DSPC), POPC, DOPC, DMPC, or natural equivalents thereof, such as soy bean PC or egg-PC, and any combination thereof.

Examples of phosphatidylethanolamines include DOPE, POPE, DPhyPE, DLinPE, DMPE, DPPE, DSPE, or natural equivalents thereof.

The lipids may be anionic. Examples of anionic lipids include, but are not limited to, the group consisting of diacylglycerolhemisuccinates, e.g. DOGS, DMGS, POGS, DPGS, DSGS; diacylglycerolhemimalonates, e.g. DOGM or DMGM; diacylglycerolhemiglutarates, e.g. DOGG, DMGG; diacylglycerolhemiadipates, e.g. DOGA, DMGA; diacylglycerolhemicyclohexane-1,4-dicarboxylic acids, e.g. DO-cHA, DM-cHA; (2, 3-Diacyl-propyl) amino}-oxoalkanoic acids e.g. DOAS, DOAM, DOAG, DOAA, DMAS, DMAM, DMAG, DMAA; Diacyl-alkanoic acids, e.g. DOP, DOB, DOS, DOM, DOG, DOA, DMP, DOB, DMS, DMM, DMG, DMA; Cholesterols and derivatives thereof, e.g. Chol-C2, Chol-C3, Chol-05, Chol-C6, Chol-C7 or Chol-C8; Chol-Cl, CholC3N or Cholesterolhemidicarboxylic acids and Cholesteryloxycarbonylaminocarboxylic acids, e.g. Chol-C12 or CholC13N, fatty acids, e.g. Oleic acid, Myristic Acid, Palmitic acid, Stearic acid, Nervonic Acid, Behenic Acid; Dioleoylphosphatidic acid (DOPA), dimethylolpropionic (DMPA), dipalmitoylphosphatidic acid (DPPA), 1-hexadecanoyl-2-(9Z-octadecenoyl)-sn-glycero-3-phosphate (POPA), 1,2-dioctadecanoyl-sn-glycero-3-phosphate (DSPA), Chol-SO4, dioleoylphosphatidylglycerol (DOPG), 1,2-ditetradecanoyl-sn-glycero-3-phospho-(1'-rac-glycerol) (DMPG), 1,2-dihexadecanoyl-sn-glycero-3-phospho-(1'-rac-glycerol) (DPPG), palmitoyloleoyl phosphatidylglycerol (POPG), 1,2-dioctadecanoyl-sn-glycero-3-phospho-(1'-rac-glycerol) (DSPG), or DOPS, 1,2-ditetradecanoyl-sn-glycero-3-phospho-L-serine (DMPS), 1,2-dihexadecanoyl-sn-glycero-3-phospho-L-serine (DPPS), 1-hexadecanoyl-2-(9Z-octadecenoyl)-sn-glycero-3-phospho-L-serine (POPS), 1,2-dioctadecanoyl-sn-glycero-3-phospho-L-serine (DSPS), or Cetyl-phosphate.

The lipids may be cationic. Examples of cationic lipids include, but are not limited to, N-11-(2,3-dioleoyloxy)propyll-N,N,N-trimethylammonium (DOTAP), 1, 2-Dimyristoyl-3-Trimethylammonium-Propane (DMTAP), 1, 2-Dipalmitoyl-3-Trimethylammonium-Propane (DPTAP), 1, 2-Dipalmitoyl-3-Trimethylammonium-Propane (DPTAP), 1, 2-Distearoyl-3-Trimethylammonium-Propane (DSTAP), Palmitoyloleoyl-3-Trimethylammonium-Propane (POTAP), 1, 2-Dioleoyl-3-Dimethylammonium-Propane (DODAP), Palmitoyloleoyl-3-Dimethylammonium-Propane (PODAP), 1, 2-Dimyristoyl-3-Dimethylammonium-Propane (DMDAP), 1, 2-Dipalmitoyl-3-Dimethylammonium-Propane (DPDAP), 1, 2-Distearoyl-3-Dimethylammonium-Propane (DSDAP), 1, 2-Dioleoyl-3-dimethylhydroxyethyl-ammonium-Propane (DODMHEAP) or 1, 2-Dioleoyl-3-dimethylhydroxyethyl-ammonium-Propane (DORI), Palmitoyloleoyl-3-dimethylhydroxyethyl-ammonium-Propane (PODMHEAP) or (PORI), 1, 2-Dimyristoyl-3-dimethylhydroxyethyl-ammonium-Propane (DMDMHEAP) or (DMRI), 1, 2-Dipalmitoyl-3-dimethylhydroxyethyl-ammonium-Propane (DPDMHEAP) or (DPRI), 1, 2-Distearoyl-3-dimethylhydroxyethyl-ammonium-Propane (DSDMHEAP) or (DSRI), 1, 2-Dioleoyl-3-methyldihydroxyethylammonium-Propane (DOMDHEAP), Palmitoyloleoyl-3-methyldihydroxyethyl-ammonium-Propane (POMDHEAP), 1, 2-Dimyristoyl-3-methyldihydroxyethyl-ammonium-Propane (DMMDHEAP), (DPMDHEAP), (DSMDHEAP), 1, 2-Dioleoyl-3-methylhydroxyethylammonium-Propane (DOMHEAP), Palmitoyloleoyl-3-methylhydroxyethylammonium-Propane (POMHEAP), 1, 2-Dimyristoyl-3-methylhydroxyethylammonium-Propane (DMMHEAP), 1, 2-Dipalmitoyl-3-methylhydroxyethylammonium-Propane (DPMHEAP), 1, 2-Distearoyl-3-methylhydroxyethylammonium-Propane (DSMHEAP), 1, 2-Dioleoyl-3-dihydroxyethylammonium-Propane (DODHEAP), Palmitoyloleoyl-3-dihydroxyethylammonium-Propane (PODHEAP), 1, 2-Dimyristoyl-3-dihydroxyethylammonium-Propane (DMDHEAP), 1, 2-Dipalmitoyl-3-dihydroxyethylammonium-Propane (DPDHEAP), 1, 2-Distearoyl-3-dihydroxyethylammonium-Propane (DSDHEAP), Dimethyldioctadecylammonium bromide (DDAB), Dioleyldimethylammonium chloride (DODAC), 1, 2-Dioleoyl-sn-Glycero-3-Ethylphosphocholine (DOEPC), 1, 2-Dimyristoyl-sn-Glycero-3-Ethylphosphocholine (DMEPC), 1, 2-Dipalmitoyl-sn-Glycero-3-Ethylphosphocholine (DPEPC), 1, 2-Distearoyl-sn-Glycero-3-Ethylphosphocholine (DSEPC), Palmitoyloleoyl-sn-Glycero-3-Ethylphosphocholine (POEPC), 1, 2-dioleyl-3-dimethyl-hydroxyethyl ammonium propane (DORIE), 1, 2-dimyristyl-3-dimethylhydroxyethyl ammonium propane (DMRIE), 1,2-Dioleoyl-3-methyl-(methoxycarbonyl-ethyl) ammonium-Propane (DOMCAP), 1,2-Dioleoyl-3-methyl-(methoxycarbonyl-methyl) ammonium-Propane (DOMGME), D0P5P, D0P6P, DC-Choi, TC-Chol, DAC-Chol, Chol-Betaine, N-methyl-PipChol, CTAB, N-[1-(2,3-dioleyloxy) propyl]-N, N, N-trimethyl ammonium chloride (DOTMA), MoChol, His-Chol, Chim, MoC3Chol, Choi-C3N-Mo3, Chol-C3N-Mo2, Choi-C4N-Mo2, Chol-DMC3N-Mo2, CholC4Hex-Mo2, DmC4Mo2, DmC3Mo2, C3Mo2, C3Mo3, C5Mo2, C6Mo2, C8Mo2, C4Mo4, PipC2-Chol, MoC2Chol, PyrroC2Chol, ImC3Chol, PyC2Chol, MoDO, MoDP, DOIM, or DPIM.

The liposome may have, for example, a diameter in a range of about 50 nm to about 500 nm, about 50 nm to about 400 nm, about 50 nm to about 300 nm, about 50 nm to about 200 nm, about 100 nm to about 200 nm, about 120 nm to about 200 nm, about 140 nm to about 200 nm, or about 140 nm to about 180 nm.

In another embodiment, the liposomes have a minimum average diameter of 20 nm. In an embodiment, the minimum average diameter is 50 nm, 100 nm, 120 nm, or 140 nm.

In another embodiment, the maximum average diameter is 500 nm. In another embodiment, the maximum average diameter is about 400 nm, about 300 nm, about 200 nm, or about 180 nm.

In one embodiment, the protein-to-lipid ratio is 1:50, 1:100, 1:200, 1:300, 1:400, 1:500, 1:600, 1:1,000, 1:10,000 or any range in between. In another embodiment, the protein-to-lipid ratio is 1:50-500. In another embodiment, the protein-to-lipid ratio is 1:50-200.

The vesicle may be made by any known means. For example, see Liposomes: A Practical Approach—Aug. 7, 2003 by Al P Williams, Oxford University Press, ISBN-10: 0199636540; ISBN-13: 978-0199636549.

Methods

In one embodiment, the present invention provides a method of identifying small molecule pharmacological agents that interfere with repolarization of cardiac cells. In one embodiment, repolarization of cardiac cells may be indirectly monitored by assaying for hERG function by utilizing vesicles having the engineered hERG protein as described above.

As used herein, small molecule pharmacological agents include any low molecular weight (<2000 daltons) organic compound that affects or regulates a biological process.

In one embodiment, the method includes reconstitution of the vesicles. As used herein, reconstitution includes the incorporation of the protein of interest (i.e., the hERG channel protein) into an artificial membrane system (e.g., the vesicles) that allows the properties of the channel to be investigated. Methods of reconstitution are known in the art. For example, reconstitution can include incorporating the engineered hERG channel protein as described above in the vesicle in the presence of KCl at a concentration from at least 150 mM, at least 200 mM, at least 250 mM, or at least 300 mM. In another embodiment, the maximum KCl concentration is about 400 mM, or about 500 mM.

The reconstituted vesicles are then diluted into a salt solution to form an assay solution. Suitable salts include NaCl, LiCl, RbCl, CsCl, and $NH_4Cl$. The concentration of the salt in the salt solution is more than 5 mM, more than 50 mM, more than 100 mM, more than 250 mM, or more than 500 mM. In another embodiment, the concentration of salt is not more than 800 mM, or not more than 1M.

After reconstitution of the vesicles containing the hERG channel and dilution into a salt solution, the vesicle is contacted with a lipophilic pH-sensitive dye by addition to the assay solution. The reconstitution of the vesicles in NaCl creates a strong gradient for the efflux of potassium.

In one embodiment, the dye is a selectively lipophilic pH-sensitive fluorescent dye that exhibits $H^+$-dependent quenching. In another embodiment, the dye includes lipophilic, weak bases, such as monoamine, diamine acridine orange (AO), and 9-amino-6-chloro-2-methoxyacridine (ACMA). These dyes are lipid permeable in their neutral forms but are non-lipid permeable or less so when protonated. Its fluorescence is quenched by pH or potential gradients across cell membranes. In a preferred embodiment, the lipophilic pH-sensitive dye is 9-amino-6-chloro-2-methoxyacridine (ACMA).

The candidate small molecule pharmacological agent is contacted with vesicle and lipophilic pH-sensitive dye by addition to the assay solution. The small molecule pharmacological agent may be added to the assay solution before, after, or in conjunction with the lipophilic pH-sensitive dye.

A baseline (first) fluorescence measurement is taken after addition of the lipophilic pH-sensitive dye. The fluorescence measurement may be taken by any known method. For example, in certain embodiments, the measurement is taken by a plate reader. In other examples, the measurement is taken by a fluorometer.

Once a baseline fluorescence measurement has been taken, an ionophore is contacted with the vesicle, pH sensitive dye, and small molecule pharmacological agent by addition to the assay solution. Addition of the ionophore allows hydrogen ion influx into the vesicle to counterbalance the loss of potassium ions as they exit the vesicle through the hERG channel because the KCl concentration creates a strong gradient for the efflux of potassium ions.

In another embodiment, the vesicle includes a hydrogen ionophore. An ionophore is a chemical species that reversibly binds ions. The term "ionophore", as used herein, denotes compounds which are capable of facilitating the transport of hydrogen ions or hydroxide ions across the liposome membrane to effect a change in pH inside the liposome membrane, and include compounds commonly referred to as proton carriers and channel formers.

Suitable ionophores include proton carriers such as nitro-, halo- and oxygenated phenols and carbonylcyanide phenylhydrazones. Preferred of such proton carriers are carbonylcyanide, p-trifluoromethoxyphenylhydrazone (FCCP), carbonylcyanide M-chlorophenylhydrazone (CCCP), carbonylcyanide phenylhydrazine (CCP), tetrachloro-2-trifluoromethyl benzimidazole (TTFB), 5,6-dichloro-2-trifluoromethyl benzimidazole (DTFB), and Uncoupler 1799 Suitable channel formers include gramicidin, alamethicin, filipin, etruscomycin, nystatin, pimaricin, and amphotericin. Other suitable proton carriers include the following compounds which preferably exhibit selectivity for cations, but will also transport protons and/or hydroxide ions: valinomycin, enniatin (type A, B, or C), beauvericin, monomycin, nonactin, monactin, dinactin, trinactin, tetranactin, antamanide, nigericin, monensin, salinomycin, narisin, mutalomycin, carriomycin, dianemycin, septamycin, A-204 A, X-206, X-537 A (lasalocid), A-23187, and dicyclohexyl18-crown-6. Such ionophores are well known in the art and are described, for example in Jain et al., Introduction to Biological Membranes, (J. Wiley and Sons, N.Y. 1980), especially pp. 192-231, and Methyl Ions In Biological Systems, ed. H. Sygel, Vol. 19, "Antibiotics And Their Complexes" (Dekker, N.Y. 1985).

In a preferred embodiment, the proton ionophore includes carbonyl cyanide m-chlorophenylhydrazone (CCCP).

The pH of the interior of the vesicle decreases as hydrogen ions enter the vesicle through the action of the hydrogen ionophore to counterbalance the efflux of potassium ions.

A second fluorescence measurement is taken after addition of the ionophore. The difference in fluorescence between the baseline measurement and the second measurement is indicative of whether the small molecule pharmacological agent inhibits hERG channel function.

In the absence of a hERG channel inhibitor, hydrogen ions enter the vesicle and lower the pH of the interior of the vesicle. As the lipophilic pH-sensitive dye passes through the lipid bilayer and enters the vesicle, the low pH in the interior of the vesicle causes protonation of the dye and quenching fluorescence. Furthermore, the protonated lipophilic pH-sensitive dye loses lipid permeability or has reduced lipid permeability. Accordingly, the lipophilic pH-sensitive dye is sequestered within the vesicle in a non-fluorescent state.

In the presence of a hERG channel inhibitor, efflux of potassium ions is impeded, and hydrogen ions do not enter the vesicle because there is no counterbalancing due to the flux of ions. Accordingly, the pH sensitive dye will pass through the lipid bilayer, but not be sequestered in the vesicle, and no significant amount of fluorescence is lost or quenched.

Accordingly, assays having no significant loss of fluorescence, or substantially similar fluorescence between the first and second measurements, indicate that the candidate small molecule pharmacological agent inhibits hERG function.

In some embodiments, substantially similar is less than a 5% reduction in fluorescence from the first and second reading and is indicative of inhibition of the hERG channel protein. In other embodiments, less than 10%, less than 20%, less than a 25%, less than a 35%, or less than a 50% reduction in fluorescence from the first and second reading is substantially similar and indicative of inhibition of the hERG channel In one embodiment, the second fluorescence measurement is taken at least 20 seconds, at least 50 seconds, at least 100 seconds, or at least 200 seconds after addition of the ionophore. In another embodiment, the second fluorescence measurement is taken at about 100-200 seconds from addition of the ionophore. In some embodiments, the second fluorescence measurement is taken at about 50-500 seconds from the addition of the ionophore.

The optimum time to take the second fluorescence reading may be determined empirically, and making such determinations is within the skill in the art. The amount of time between addition of the ionophore and taking the second fluorescence reading should be long enough to visualize the desired effect.

In some embodiments, the method of assaying hERG function includes comparison of the fluorescence of the assay mixture described above with that of a reference sample, e.g., DMSO. In this embodiment, the vesicles containing the hERG channel are reconstituted as described above, a pH-sensitive dye (as described above) is added to the assay solution, a candidate small molecule pharmacological agent is added, and an ionophore is added, providing a test sample.

The fluorescence measurement of the test sample is compared against a reference sample that includes everything except the small molecule pharmacological agent.

In some embodiments, the fluorescence measurement is taken at least 50 seconds, at least 100 seconds, or at least 200 seconds after addition of the ionophore. In other embodiments, the fluorescence measurements are taken at about 100-200 seconds from addition of the ionophore. In some embodiments, the fluorescence measurements are taken at about 50-500 seconds from the addition of the ionophore.

In some embodiments, more than a 10% difference in fluorescence between the test sample and the reference sample is indicative of inhibition of the hERG channel In other embodiments, more than a 25%, more than a 35%, more than a 50%, or more than a 75% difference in fluorescence between the test sample and the reference sample indicates inhibition of the hERG channel In some embodiments, the effect of a candidate small molecule pharmacological agent on a hERG channel may be characterized by looking at the graphical representation of the data generated from the fluorescent measurements from the above-described method over time.

Figure 2A:
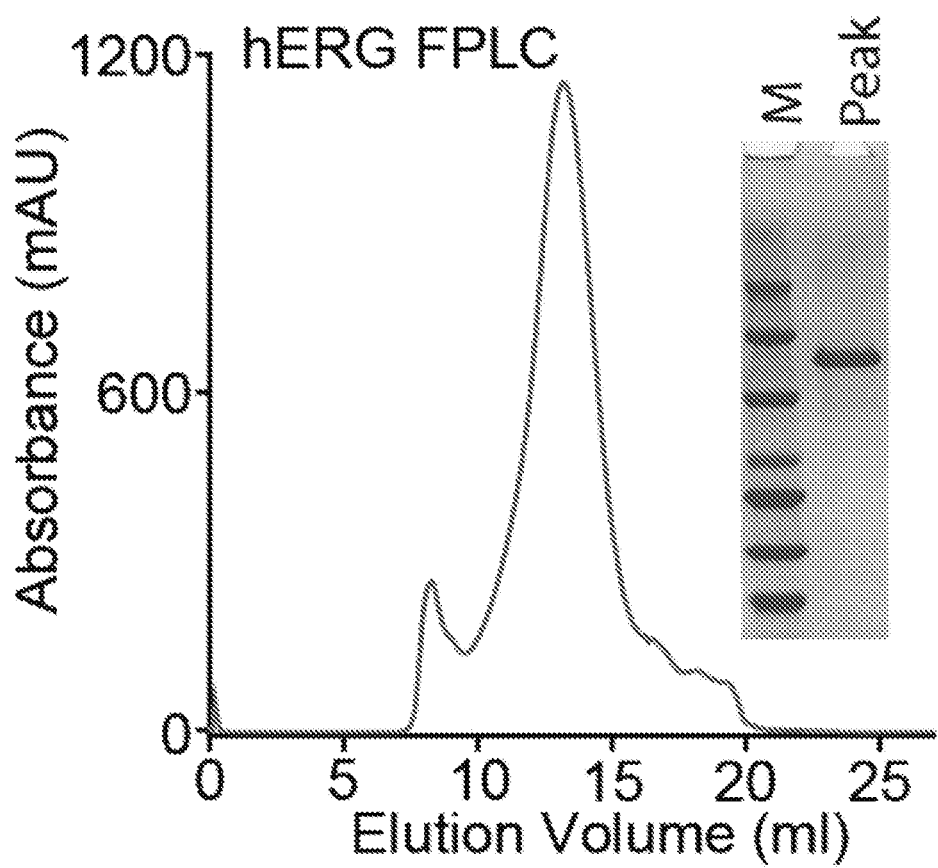
FIGS. 2A-2G. Development and validation of a new hERG assay. (2A) A hERG mutant channel with internal deletions of unstructured cytoplasmic loops (residues 141-380 and 871-1005) was engineered. This mutant channel protein ran as a mono-disperse FPLC peak on gel filtration and as a single band on SDS-PAGE. (2B) Protein-to-lipid ratio titration of hERG in LFA showing that 1:100 provided a good signal for drug safety testing. (2C-2D) Normalized titration of dofetilide and astemizole, two well-characterized hERG blockers. The LFA IC50 values correlate well with electrophysiological recordings, although are around 10-fold higher (see methods). (2E) Dose response curves derived from LFA (n=3 each). (2F) LFA IC50 values were plotted against patch recording IC50 values reported in the literature (the lowest affinity IC50 values were used if a range of IC50 values were reported by patch clamp). No false negatives were found. The plot was fitted with linear regression in OriginPro. All data are mean±SEM. (2G) Simulated blocker dose response of the K⁺ channel conductance and the total conductance in the LFA. Normalized K⁺ conductance $G_{Knorm}=G_{K0}\times(1-x/(K_d+x))/G_{K0}$ is plotted as dashed line assuming an equilibrium dissociation constant of $K_d$=10 nM. $G_{K0}$ is the conductance of the potassium channel without blocker and x is the blocker concentration. Normalized total conductance (solid line) is given by $G_{totnorm}=G_{tot}/(G_{K0}^{-1}+G_{H}^{-1})^{-1}$ where $G_H$ is the conductance of the H⁺ ionophore CCCP and $G_{tot}$ is the total conductance as defined in equation (3). $G_H$ is set to 1 and $G_{K0}$ to 10 for simplicity. The blocker concentration to reduce the normalized total conductance by half is 110 nM compared to the equilibrium dissociation constant of $K_d$=10 nM for the K⁺ conductance. Thin dotted lines are plotted to emphasize this shift in the blocker concentration to achieve half block.
Figure 2B:
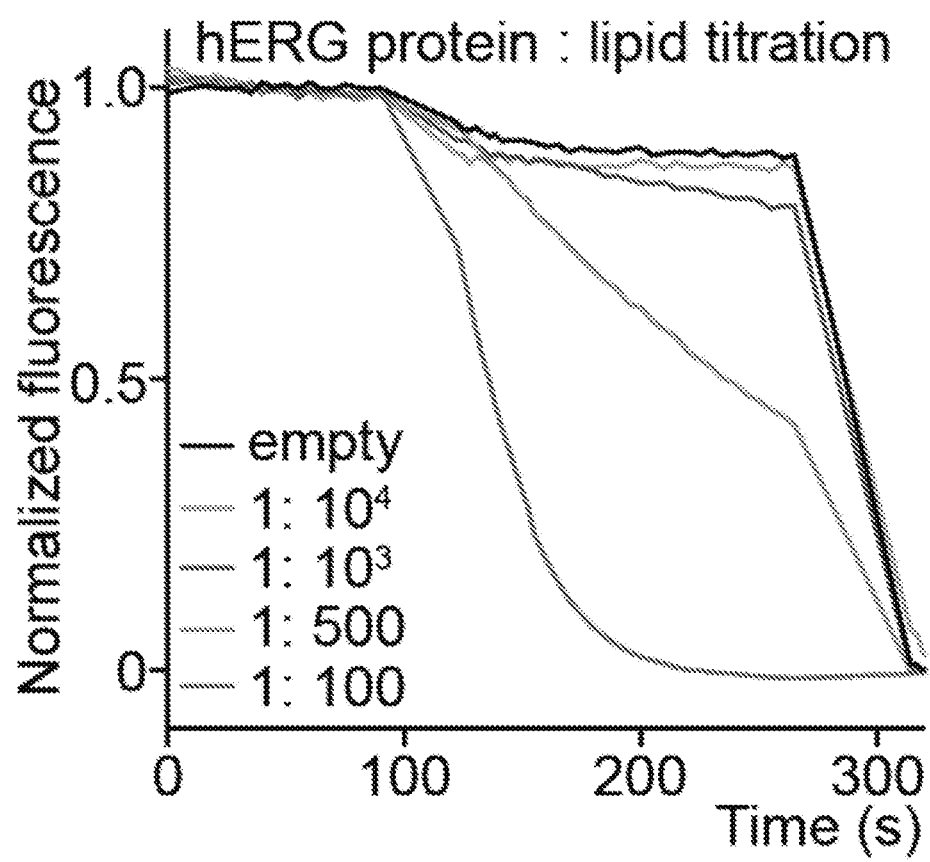
Figure 2C:
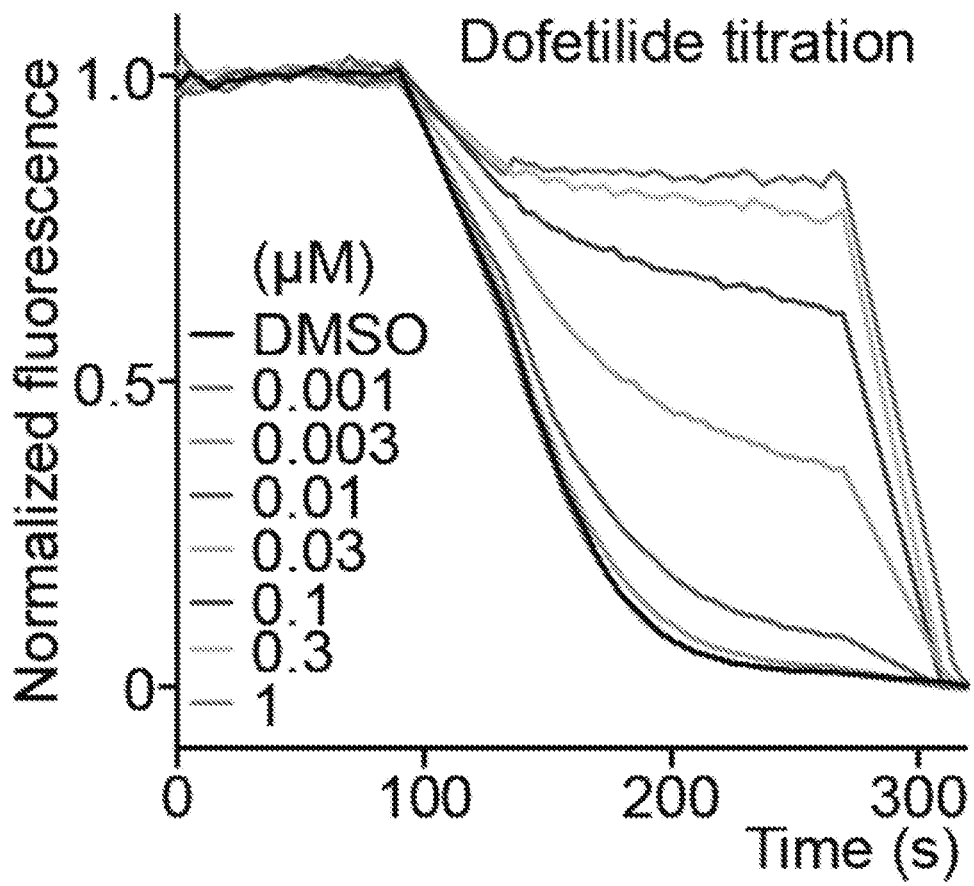
Figure 2D:
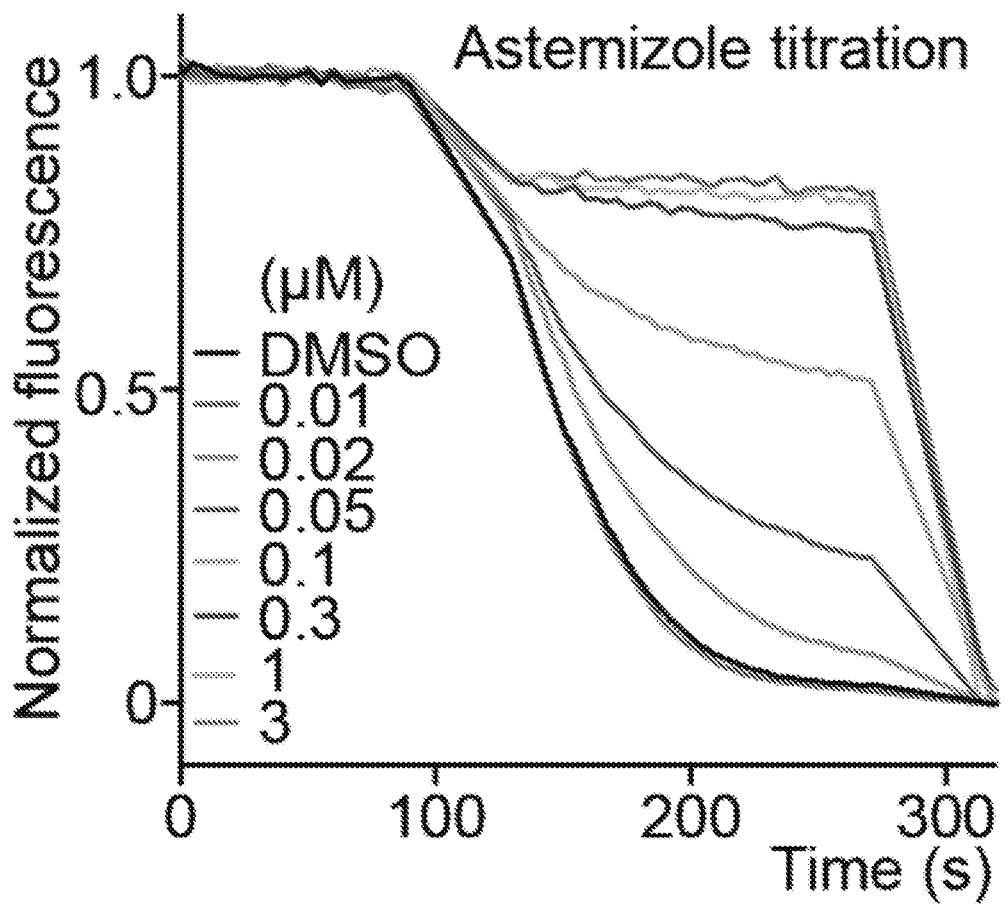
Figure 2E:
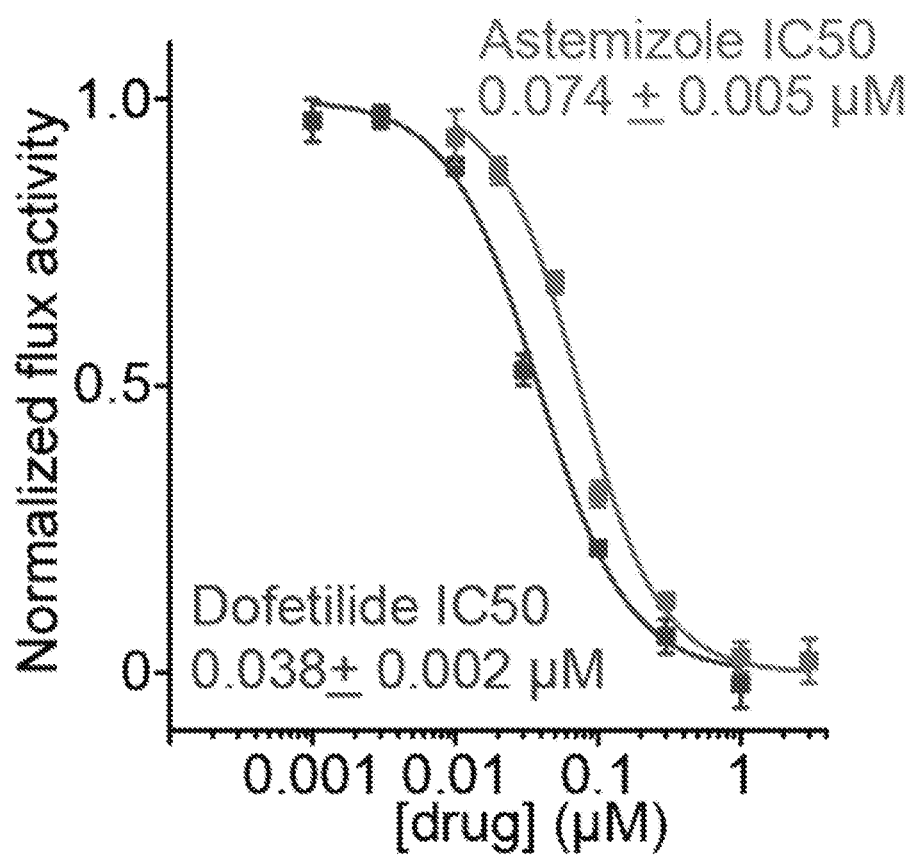

Applicants have tested small molecule pharmacological agents that are known inhibitors (FIGS. 2C, 2D, and 3) of the hERG channel and agents that are known non-inhibitors of the hERG channel (FIG. 4). The results were displayed on a graph, with time on the X-axis and level of fluorescence on the Y-axis for various doses of the respective small molecule pharmacological agent, typically, between 0.01 µM and 100 µM. Small molecule pharmacological agents that are known to inhibit the hERG channel will exhibit a shift in the shape of the curve as the concentration of the agent is increased. See FIGS. 2C, 2D, 3, and 5. In particular, the curve shifts from a sigmoidal shape to a more linear or gradually sloping straight line. This is because agents that inhibit the hERG channel, at a certain dose, impede the efflux of potassium ions through the channel, thereby minimizing protonation of the dye and quenching fluorescence. In contrast, agents that do not affect the hERG channel do not have any significant effect on the shape of the curve in the presence of the agent. This is exemplified in FIG. 4, where 100 µM of a known non-inhibitor has no effect on the shape of the curve. In particular, the shape of the curve remains sigmoidal.

In view of the foregoing, the slope of the curve can be analyzed for the loss of fluorescence to determine whether the small molecule pharmacological agent has an effect on the hERG channel As used herein, the slope of the curve is the slope of the linear range of the curve.

In the absence of a hERG channel inhibitor, the slope of the line is greater than the slope of the line in the presence of a hERG channel inhibitor. As an example, see FIG. 2C. In particular, the slope of the linear range in the absence of dofetilide (DMSO) is larger than the slope of the linear range with 1 µM dofetilide.

As used herein, larger means more than 1.5 times larger, more than 2 times greater, more than 3 times greater, or more than 5 times greater.

In the absence of a hERG channel inhibitor, the slope of the line is substantially similar between vesicles treated with a small molecule pharmacological agent and those untreated.

In some embodiments, a potassium ionophore is added after addition of the ionophore to allow potassium channel-independent efflux, to exclude false positive compounds with strong auto-fluorescence or causing vesicle lysis. In some embodiments, the potassium ionophore is valinomycin.

Valinomycin addition causes little change in ACMA fluorescent signal under conditions where the channels are active, but it causes a sharp drop in signal under conditions where the channels are blocked or inactive. This is an important control since fluorescent compounds may be identified as inhibitors in the primary screen, but these are likely false positives if the fluorescent signal does not decrease after valinomycin addition. Similarly, compounds that lyse the vesicles may show up as false positives in the primary screen, and can be discarded after an anomalous post-valinomycin result.

When valinomycin is added, another fluorescence measurement is taken. The fluorescence measurement may be taken at least 10 seconds after addition of valinomycin. In some embodiments, the fluorescence measurement is taken at least 30 seconds, at least 60 seconds, at least 100 seconds, or at least 200 seconds after addition of valinomycin.

In some embodiments, more than a 50% loss in fluorescence after addition of valinomycin is indicative of inhibition of the hERG channel In other embodiments, more than 75%, more than 80%, more than 90%, or more than 95% loss in fluorescence after addition of valinomycin indicates inhibition of the hERG channel.

In another embodiment, the method is performed in a high-throughput format. In one embodiment, the method is performed in a multi-well plate. The multi-well plate includes at least 96 wells, at least 384 wells, or at least 1536 wells.

EXAMPLES

The present disclosure may be better understood with reference to the examples, set forth below. The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure.

Results
Assay Description

Figure 1B:
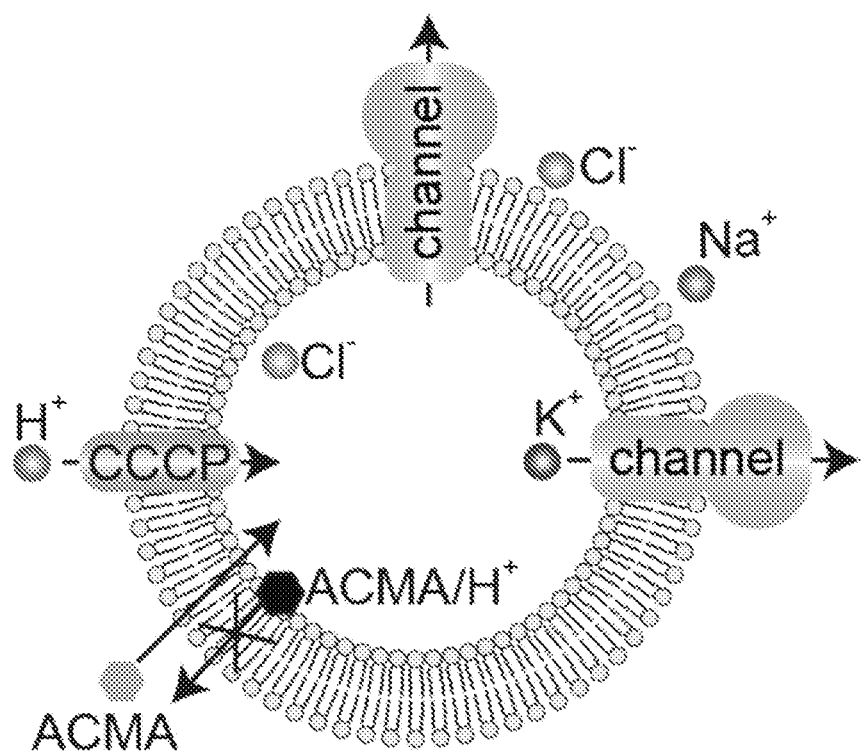
Figure 1C:
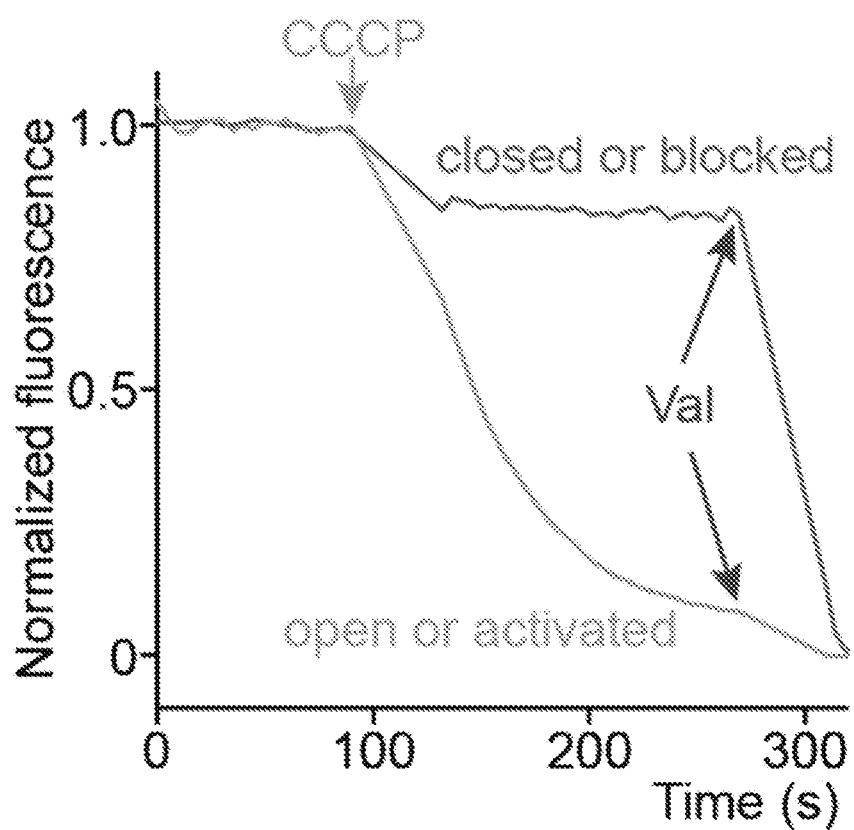
Figure 1D:
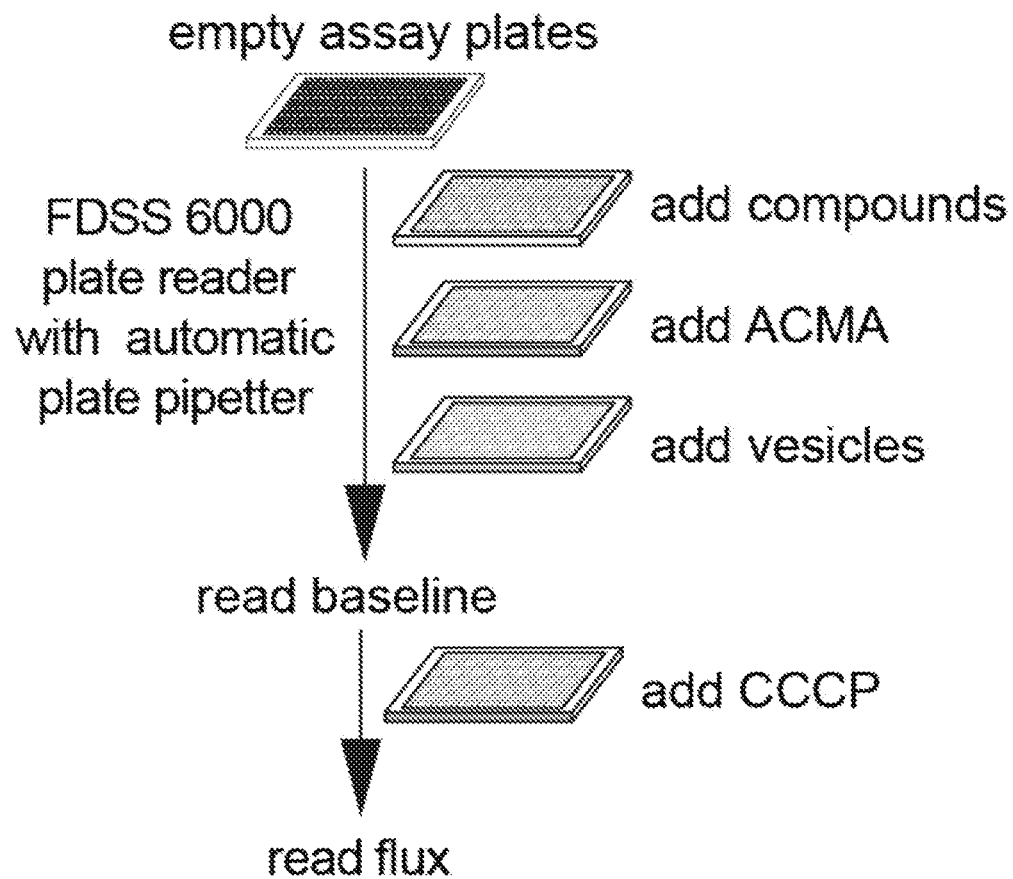

The principle of the assay is illustrated in FIG. 1B. Purified $K^+$ Channels are reconstituted into lipid vesicles in the presence of KCl ranging in concentration from 150 mM to 300 mM. The channel-containing vesicles are usually frozen for storage at this stage. To assay, thawed vesicles are diluted into a NaCl solution, which creates a strong gradient for the efflux of $K^+$. Potassium efflux is initiated by the addition of the $H^+$ ionophore carbonyl cyanide m-chlorophenylhydrazone (CCCP), which allows influx of $H^+$ to counterbalance the efflux of $K^+$. The $H^+$ influx is monitored by the $H^+$-dependent quenching of a fluorescent dye, 9-amino-6-chloro-2-methoxyacridine (ACMA). In the example shown in FIGS. 1B and 1C, $K^+$ efflux leads to dye quenching when $K^+$ channels are active (light grey trace), but not when they are inhibited (red trace). The $K^+$ ionophore valinomycin is finally added to allow $K^+$ channel-independent efflux. For many $K^+$ Channels, assay conditions under which the channels are inactive can be found in order to screen for activators that will initiate $K^+$ efflux. FIG. 1D illustrates the sequence of additions used in a multi-well plate format and FIG. 1C shows an example of the data read-out.

Constructs

DNA fragments encoding different constructs were amplified by PCR using Phusion DNA polymerase (New England Biolabs) and cloned into expression vectors modified by the MacKinnon lab for yeast, insect and mammalian cells. All constructs were confirmed by sequencing (Genewiz).

Protein Purification
Human ERG (hERG) Purification

The GFP-tagged hERG truncation mutant was cloned into a BacMam vector modified from pEG[23] (a generous gift from Prof. Eric Gouaux, Vollum Institute) for expression in HEK293S GnTI⁻ cells (ATCC). hERG virus production followed the BacMam virus protocol[23]. HEK293S GnTI⁻ cells were cultured in FreeStyle 293 Expression Medium (Life Technologies) supplemented with 2% FBS and 1% penicillin/streptomycin in incubators (Thermo, model 3950) equipped with tabletop orbital shaker (Thermo, MaxQ HP) at 130 rpm and 37° C. with moisture and 8% $CO_2$. Cells were infected with hERG virus at a density of 3×10⁶ cells/ml. 24 h after infection, 10 mM sodium butyrate (sigma) was added to induce protein expression. 36 h after induction, cells were harvested by centrifugation, frozen with liquid nitrogen, and stored at −80° C.

All steps were performed at 4° C. Frozen HEK293S GnTI⁻ cells expressing hERG channel protein were lysed in hypo-osmotic lysis solution (10 mM Hepes-NaOH, pH 7.4, 30 mM KCl, 5 mM DTT, 20 µg/ml DNase, a protease inhibitor cocktail containing 1 µg/ml leupeptin, 1 µg/ml pepstatin, 1 µg/ml aprotinin, 100 µg/ml soy trypsin inhibitor, 1 mM benzamidine, 100 µg/ml 4-(2-Aminoethyl) benzenesulfonyl fluoride and 1 mM phenylmethysulfonyl fluoride) at a ratio of 1 g cell pellet/4 mL lysis buffer.) by stirring to homogeny. Cell lysates were centrifuged at 16,000 rpm for 45 mM to collect membranes. Membrane pellets were re-suspended in extraction buffer (20 mM Hepes-NaOH, pH 7.4, 300 mM KCl, 20 µg/ml DNase, a protease inhibitor cocktail, 1% DDM, 0.2% Cholesteryl hemisuccinate (CHS, Anatrace)) and extraction continued for 1 h. Extracts were collected by centrifugation at 20,000 g for 15 mM Washed GFP-nanobody resin (CNBr-activated Sepharose 4B (GE Healthcare) conjugated with a GFP-binding nanobody[24,25]) was added to the supernatant (5 mL resin/1 L cell) and binding continued for 1 h with rotation. After binding, resin was collected at 1,000 rpm for 5 mM and washed briefly with wash buffer (20 mM Hepes-NaOH, pH 7.4, 300 mM KCl, 0.1% DDM, 0.02% CHS, 0.1 mg/ml lipids (1-palmitoyl-2-oleoyl-sn-glycero-3-phosphoethanolamine (POPE): 1-palmitoyl-2-oleoyl-sn-glycero-3-phosphocholine (POPC): 1-palmitoyl-2-oleoyl-sn-glycero-3-phosphate (POPA)=5:5:1). Resin was loaded onto a column and further washed with 20 cv wash buffer. PreScission protease (~1:40 wt:wt) was added to washed resin and on-column cleavage continued for 1.5 h with gentle rotation. Cleaved protein was eluted in wash buffer, concentrated (100 kDa MWCO), and applied to a Superose 6 column equilibrated in SEC buffer (20 mM Hepes-NaOH, pH7.4, 300 mM KCl, 0.1% DDM, 0.02% CHS, 0.1 mg/ml lipids (POPE:POPC:POPA=5:5:1), 0.5 mM tris(2-carboxyethyl)phosphine (TCEP), 10 mM DTT). Peak fractions containing hERG channel protein were pooled for reconstitution.

Proteoliposome Reconstitution

Lipids in organic solvent were handled with glass pipettes and vials. 10 mg/ml POPE and POPG (1-palmitoyl-2-oleoyl-sn-glycero-3-phospho-(1'-rac-glycerol)) from Avanti in chloroform were mixed (with a ratio of 3:1 wt:wt) and aliquoted in 4 ml per glass vial (Kimble Chase, 16×125 mm). Lipid aliquots were air-dried under argon, washed with pentane, and dried again under argon in a laboratory chemical hood. Lipids were protected from light by wrapping with aluminum foil and protected from oxidation by topping with argon in all subsequent steps. Lipids were further dried overnight in a vacuum chamber with loose caps on the vials. Each dried aliquot was re-hydrated in 2 ml reconstitution buffer (20 mM Hepes-KOH, pH7.4, 1 mM EDTA, 150 mM KCl, except for hERG 300 mM KCl were used). Lipid solutions were sonicated until translucent in a bath sonicator (Laboratory Supplies, model G112SP1T) with multiple cycles of 1 mM on and 1 mM off to prevent overheating. Sonicated lipid solutions were mixed with an equal volume of solubilization buffer (reconstitution buffer with 20 mM DM and 20 mM DTT) and incubated for 30 mM by rotating. Solubilized lipid-detergent solution was mixed with purified protein at desired ratios and incubated for 1 hour at room temperature by rotation. After incubation, protein-lipid-detergent solution was immediately transferred to 50 kDa MWCO dialysis bags (Spectrum Labs) in cold reconstitution buffer with fresh 3 mM DTT and dialyzed at 4° C. (4 L buffer/20 ml protein-lipid-detergent solution). Reconstitution buffer was changed every 12 hours for 6 cycles. After visible vesicle formation, bags were massaged manually each day to break up large lipid aggregates. Pre-wetted Bio-Beads SM2 (Bio-Rad, first wetted in methanol, subsequently washed 5 times with ddH$_2$O and 1 time with reconstitution buffer) were added to reconstitution buffer (5 ml/4 L buffer) for the last three cycles to remove residual detergents. 50 μL aliquots of the proteoliposomes were flash-frozen in liquid nitrogen, and stored in −80° C.

High-throughput LFA Screens

Compound library collections: 300,000 compounds were collected for screening, of which 100,000 were from Enamine (a pre-plated diverse subset of their library), 100,000 were from ChemBridge (DIVERSet-EXP and DIVERSet-CL), and 100,000 were from the library available at The Rockefeller University High-Throughput and Spectroscopy Resource Center (RU-HTSRC). The compounds were selected to maximize diversity. These compounds were stored frozen in DMSO at −20° C. in 384-well stock plates at the concentration of 5-10 mM in aliquots. On the day of screening, drug DMSO plates were thawed and small volume of drugs were pipetted out and diluted into screening drug plates filled with drug buffer by robot. The same screening drug plate served multiple K$^+$ Channel assays, which reduces the cost of the screens.

The primary screen: The primary screen was carried out with a FDSS6000 (Hamamatsu) plate reader with automatic pipetting in 384-well format. Before screening, flat-bottomed 384-well plates (Greiner Bio-One, cat. 781076) were filled with stock solutions of different components including drugs, ACMA, and CCCP. Vesicles were added to v-bottomed 384-well plates (Greiner Bio-One, cat. 784201). Drug stock plates were filled with 2.5 μM screening compounds in drug buffer (675 mM NaCl, 20 mM Hepes-NaOH, pH7.4). Columns 23 and 24 were positive and negative control drugs, respectively. ACMA stock plates were filled with 6.5 μM ACMA in ACMA buffer (20 mM Hepes-NaOH, pH7.4). CCCP stock plates were filled with 16 μM CCCP in a buffer (5 mM EDTA, 20 mM Hepes-NaOH, pH7.4). Vesicles containing different channel proteins were thawed in a 37° C. water bath for 30 min and briefly mixed to homogeny by gentle pipetting. Thawing at 37° C. is very critical in obtaining robust LFA signals. Homogeneous vesicles were left at room temperature until immediately before the screening. Vesicles were diluted into a buffer containing no K$^+$ (150 mM NaCl, 20 mM Hepes-NaOH) before their addition to the stock plate in order to create a stronger K$^+$ gradient across the vesicle membrane, enhancing the flux signal. Vesicles were stable in high K$^+$ solution for at least a day but gradually lost flux activity in low K$^+$ high Na$^+$ buffers, we therefore waited until right before the screen to dilute the vesicles. Vesicles in stock plates maintained their robust flux signals for at least 20 consecutive plates screened. Empty 384-well clear-bottom plates (Greiner Bio-One, cat. 781096) were used as assay plates to mix flux components and to read fluorescence.

Drug stock plates were loaded to the back port of FDSS6000 and empty assay plates were loaded to the front port. ACMA stock plates, vesicle stock plates, and CCCP stock plates were placed on the rotating stage automatically controlled by FDSS6000. Pipettes loaded on the pipette header of FDSS6000 were automatically washed before and after each pipetting. The assay was performed at room temperature.

The FDSS6000 pipetted and mixed 12 μl of drug solution, 6 μl of ACMA solution, and 6 μl of vesicle solution into an assay plate, and the baseline fluorescence was recorded (using 380 nm excitation and 510 nm emission). Then 6 μl of CCCP was added and mixed to initiate the K$^+$ flux and the fluorescent signal was monitored every 5 seconds for 55 cycles. No valinomycin was used during the primary screen because it adhered to the pipette tips and contaminated subsequent plates. The final concentrations for the components in the LFA reaction were 1 μM drug, 1.3 μM ACMA, and 3.2 μM CCCP.

Hit Confirmation using LFA: Once the primary screens were finished and primary hits were selected using offline data analysis, the hits were confirmed using a fluorescent plate reader (Tecan, Infinite M1000 with excitation wavelength 410 nm and emission wavelength 490 nm) with manual pipetting following the same protocol as the primary screen in 384-well plates. After monitoring the flux signal for 55 cycles, 1 μl of 8 μM valinomycin (in DMSO) was added to allow K$^+$ ions to pass through the membrane and reach equilibrium. The final fluorescence value was then recorded. Valinomycin addition causes little change in ACMA fluorescent signal under conditions where the channels are active, but it causes a sharp drop in signal under conditions where the channels are blocked or inactive. This is an important control since fluorescent compounds may be identified as inhibitors in the primary screen, but these are likely false positives if the fluorescent signal does not decrease after valinomycin addition. Similarly, compounds that lyse the vesicles may show up as false positives in the primary screen, and can be discarded after an anomalous post-valinomycin result.

Once the hits were confirmed, fresh compounds were purchased from the same vendors that had supplied the primary screening compounds and drug titrations were conducted. Each compound titration was performed in a single column of a 384-well plate to ensure the simultaneous addition of CCCP using a multichannel pipette in a Tecan Infinite M1000 plate reader. The flux data were normalized, plotted, and fitted as detailed in Data Analysis section.

Explanation of the IC50 Offset in the hERG Assay

In LFA efflux of $K^+$ is coupled to ionophore-mediated influx of $H^+$. Through analysis of efflux rates as a function of protein-to-lipid ratio with various $K^+$ Channels we know that under many circumstances (specific channels such as hERG and at high protein-to-lipid ratios), when $K^+$ channels are not blocked, the influx of $H^+$ limits the efflux of $K^+$. Consequently, reduced $K^+$ efflux is observed only when $K^+$ Channels are sufficiently blocked to allow $K^+$ efflux to become rate limiting. This effect causes an offset in the estimate of the IC50 of a $K^+$ channel blocker. To demonstrate with a simple model how this occurs we model the processes of $K^+$ efflux and $H^+$ influx as conductors in series, $G_K$ and $G_H$. Therefore, total conductance is $$G_{tot} = (G_K^{-1} + G_H^{-1})^{-1}, \quad (1)$$

Figure 2F:
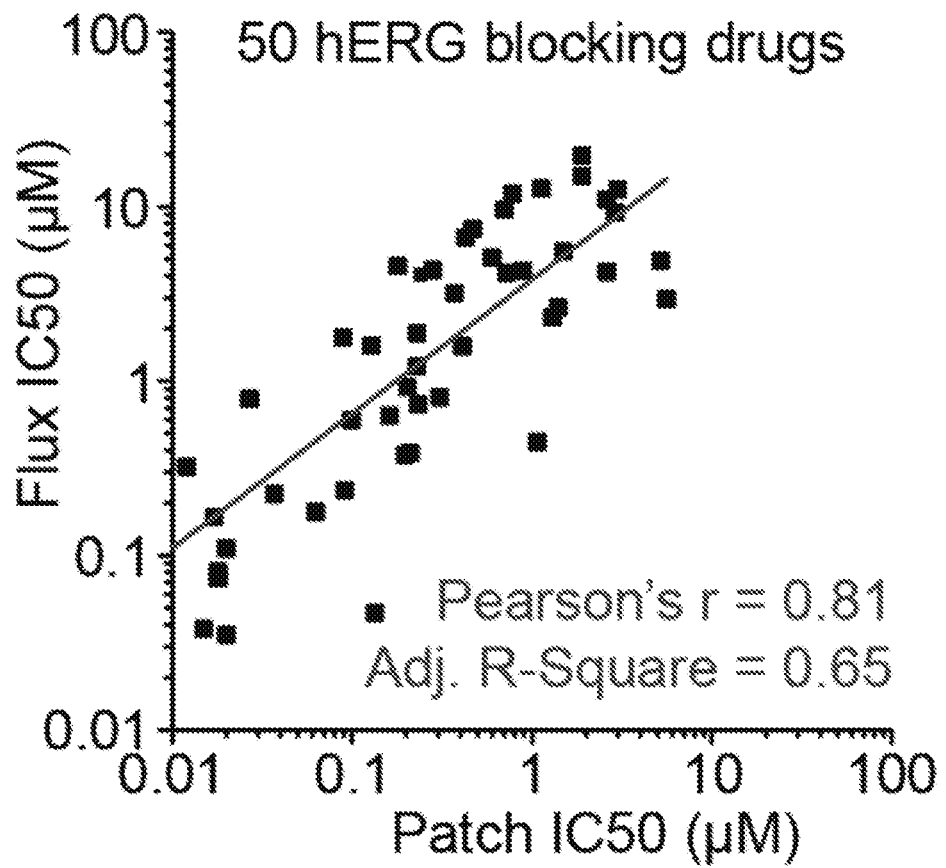
Figure 2G:
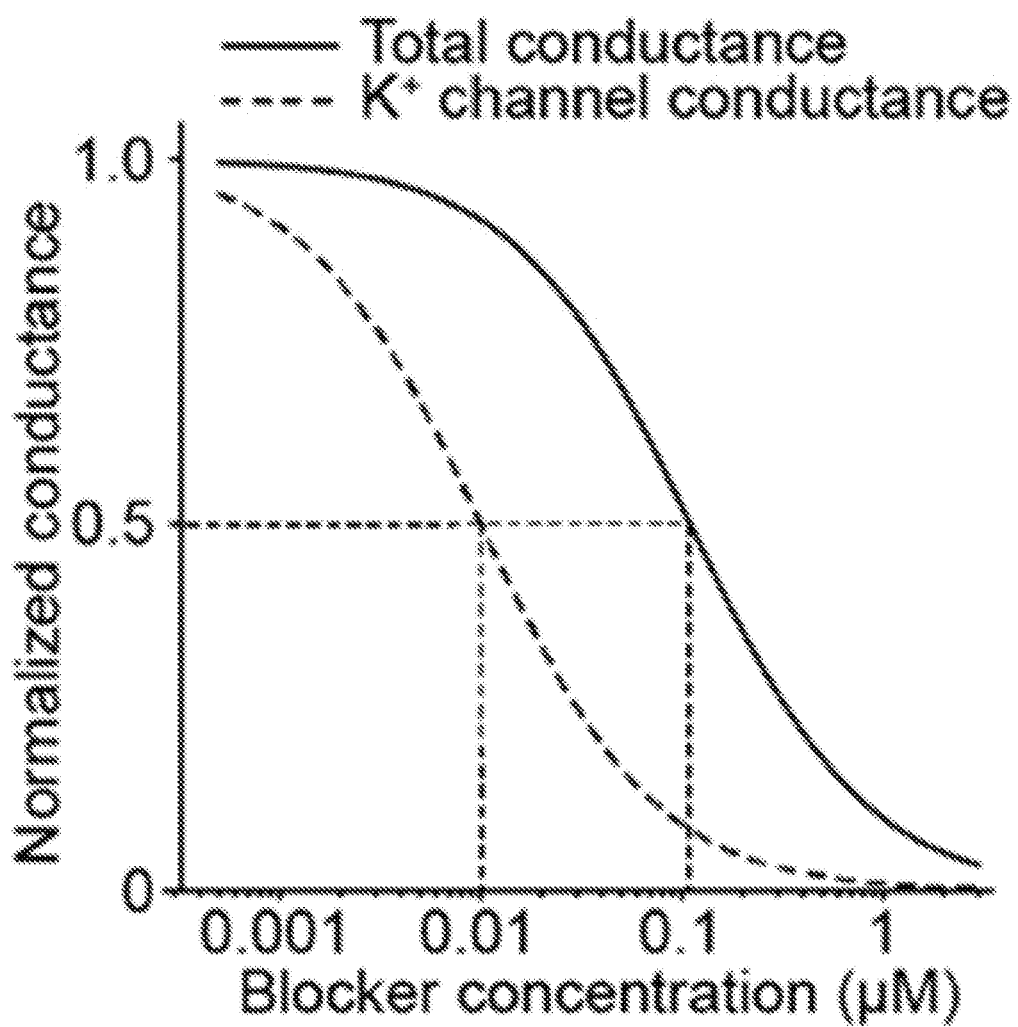
Figure 3B:
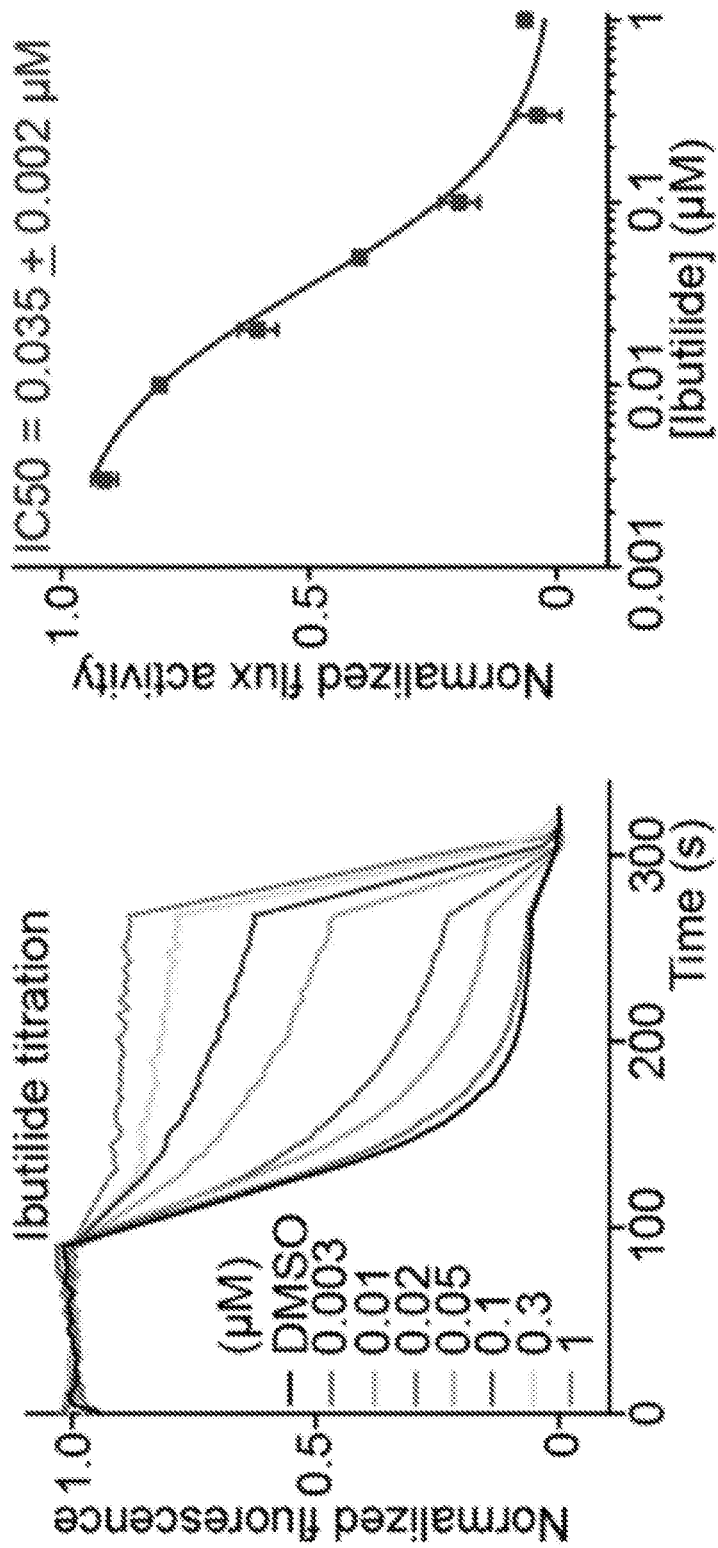
Figure 3C:
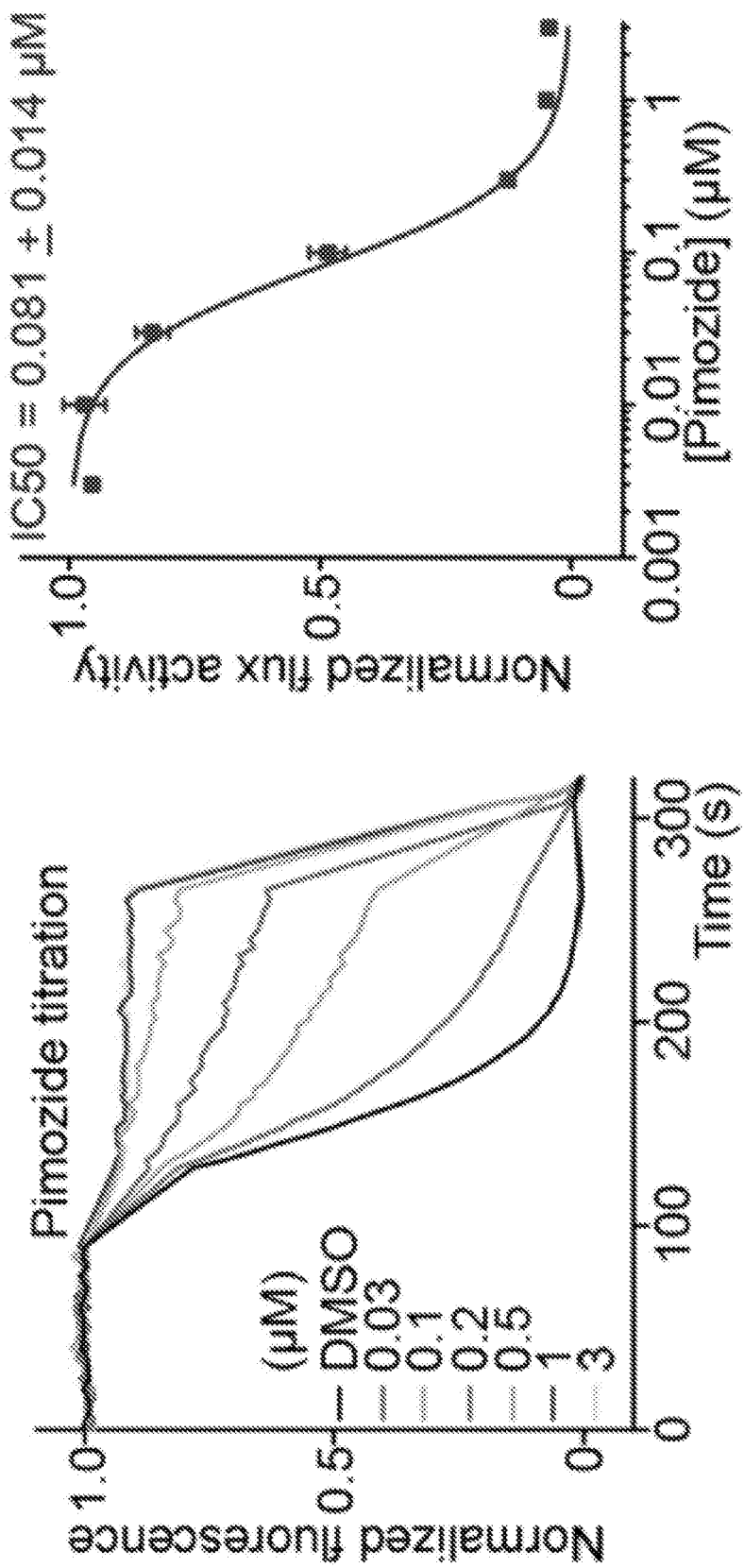
Figure 3D:
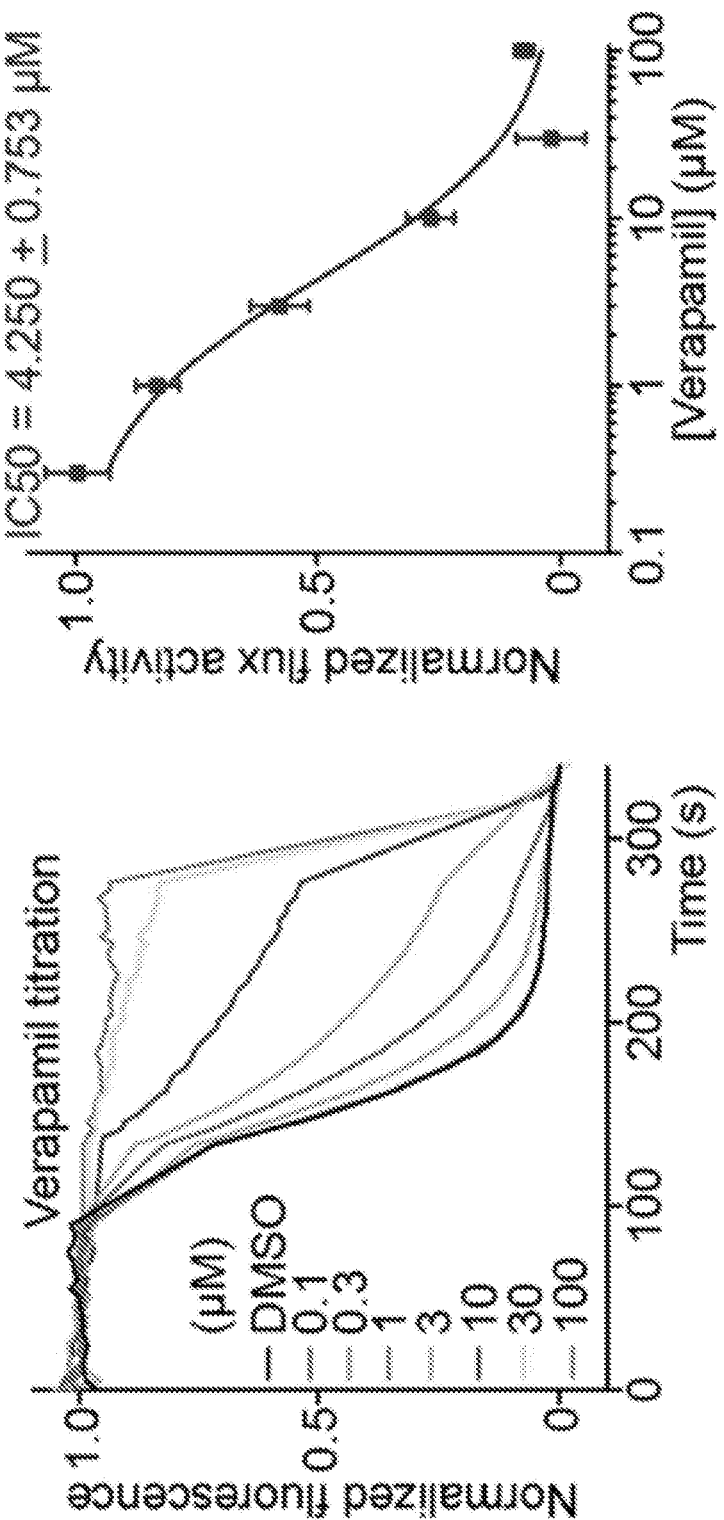
Figure 3E:
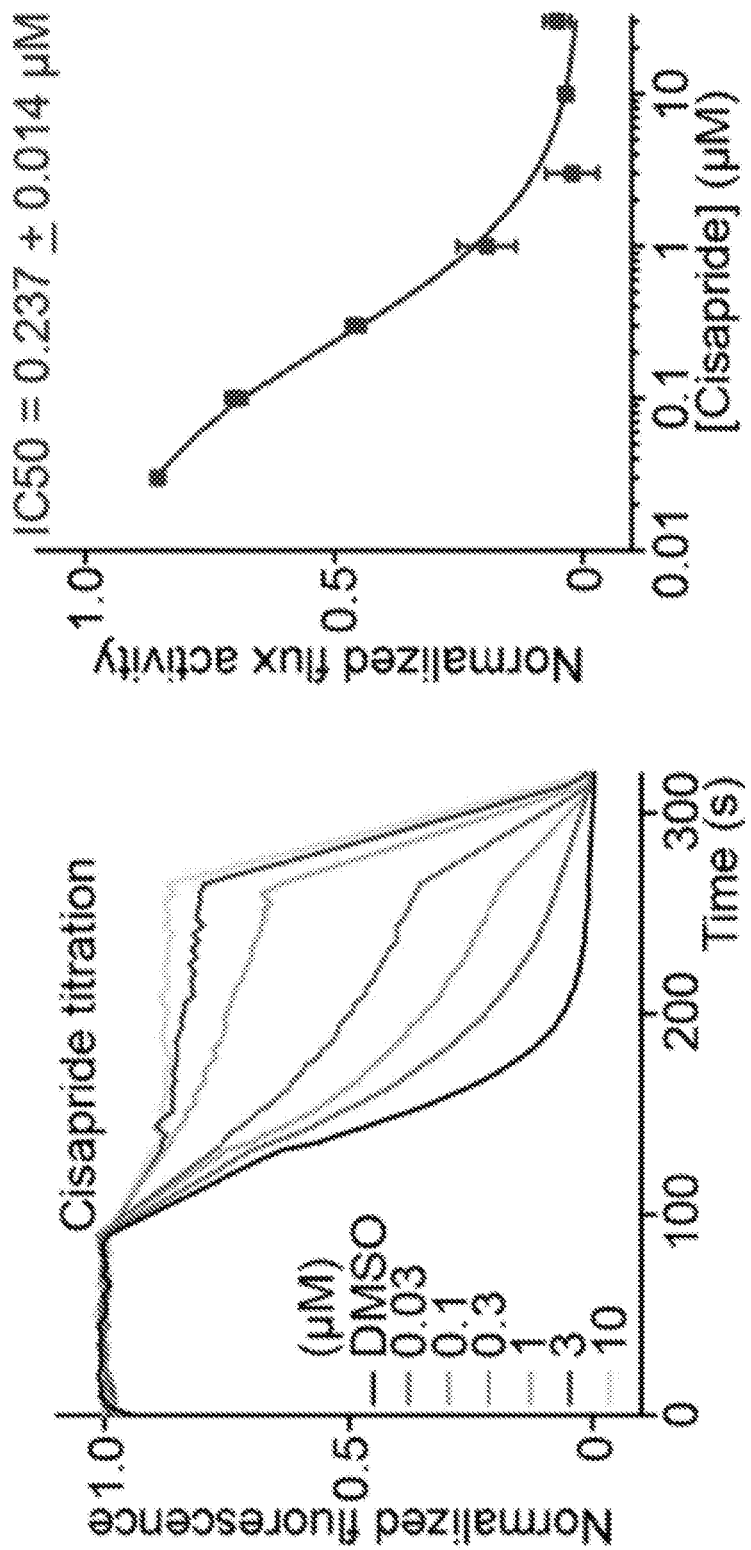
Figure 3F:
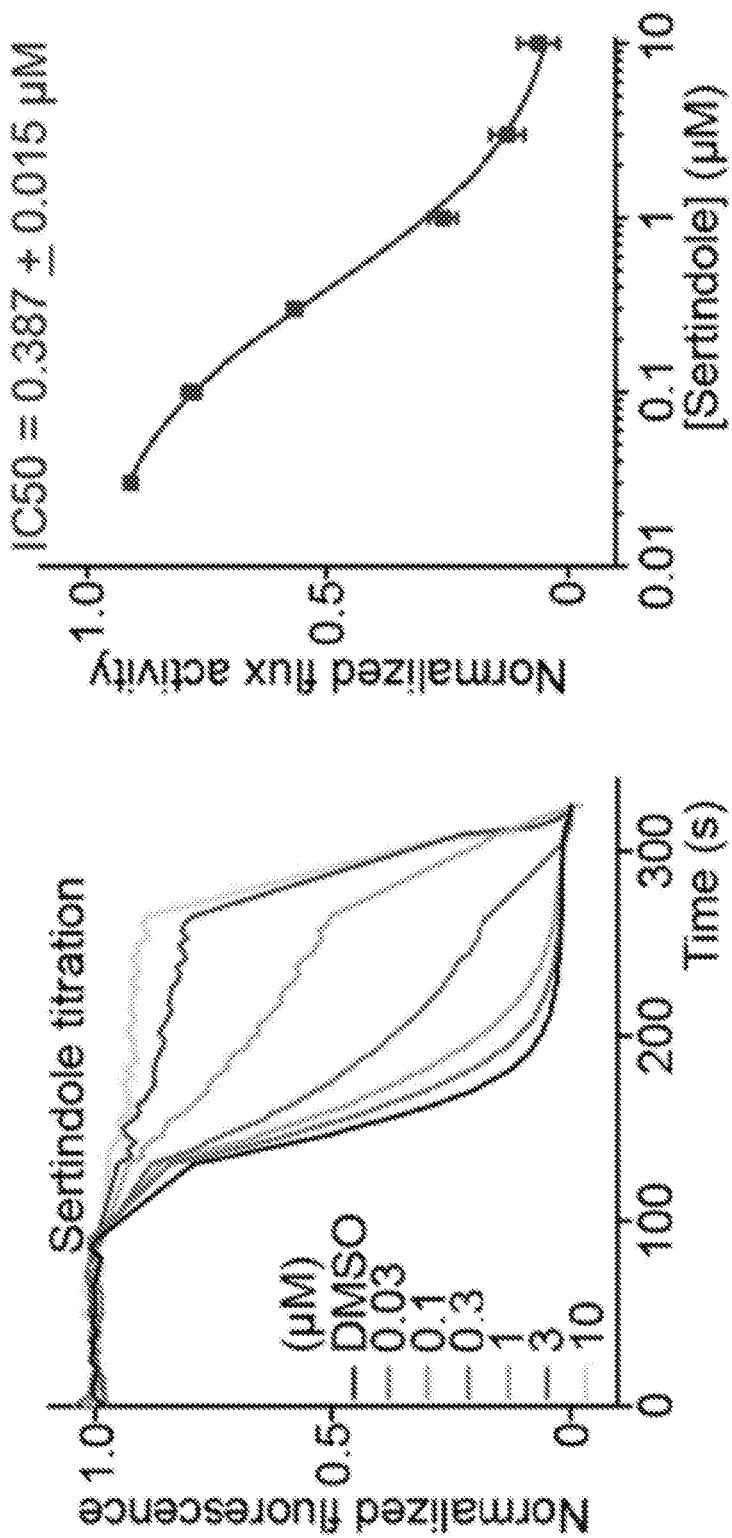
Figure 3G:
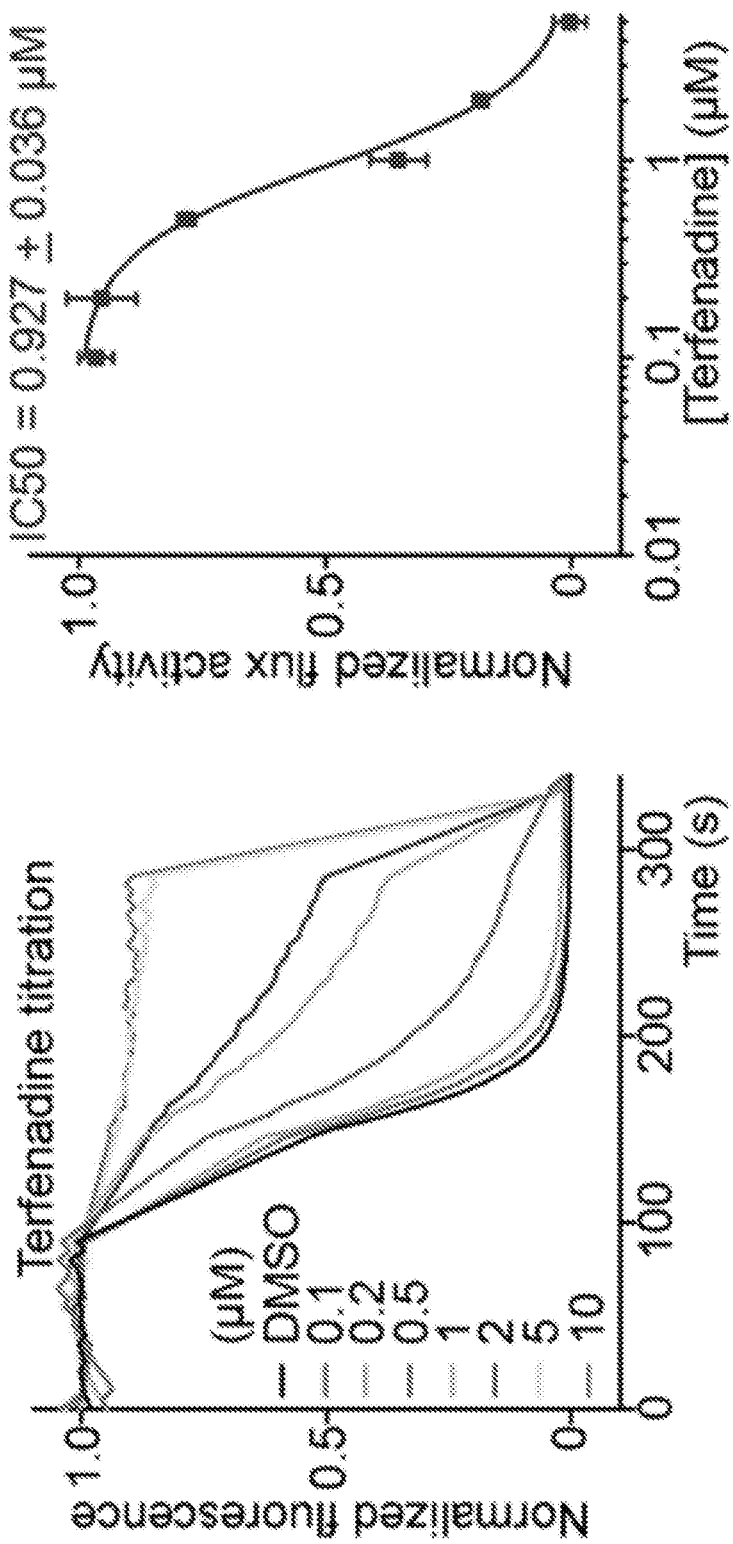
Figure 4A:
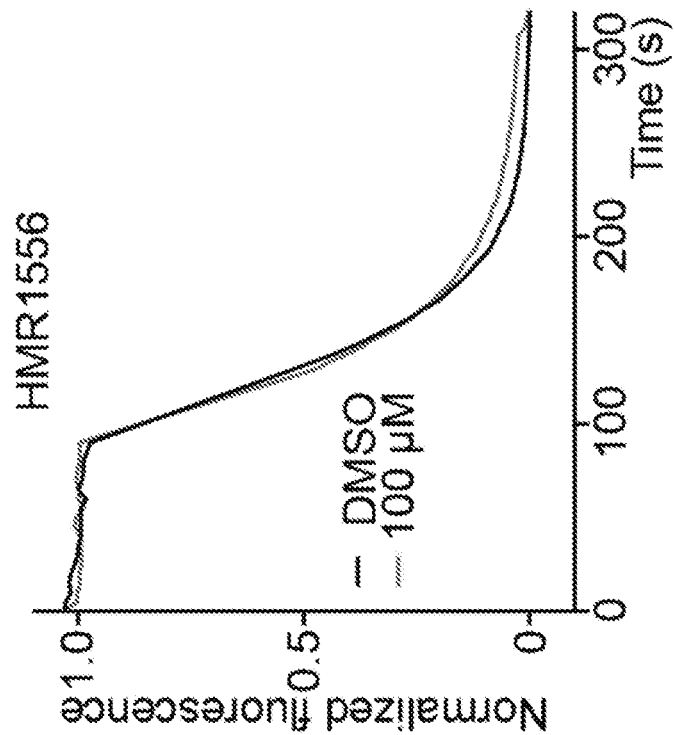
Figure 4B:
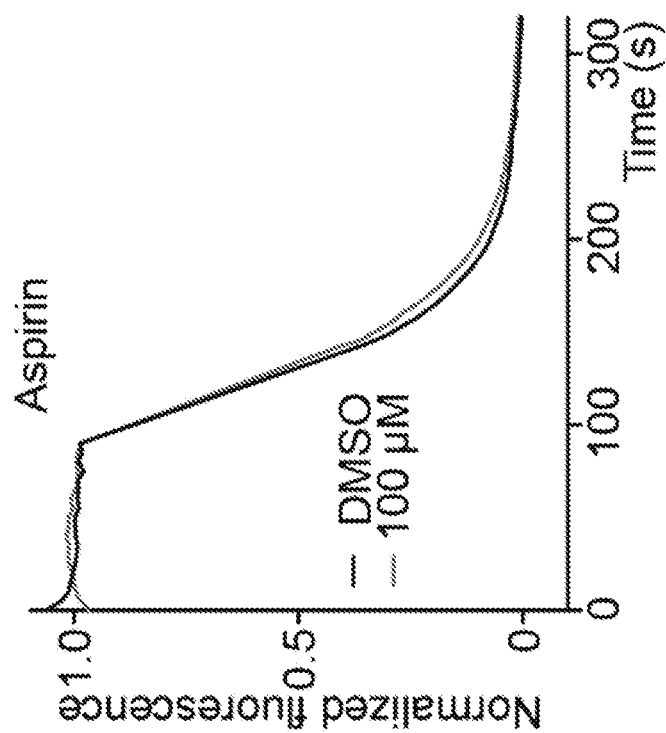
Figure 4D:
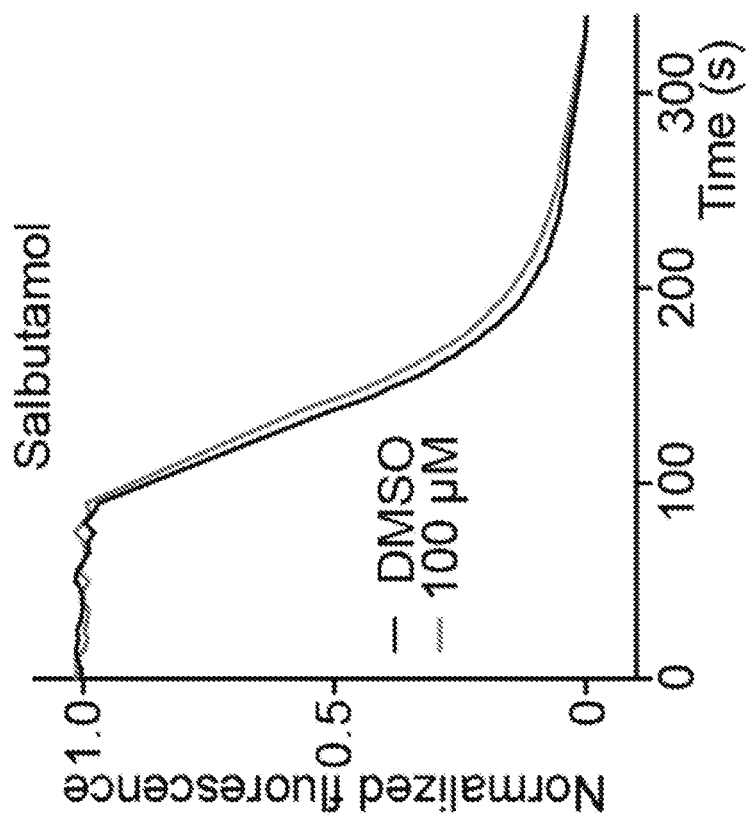
Figure 4C:
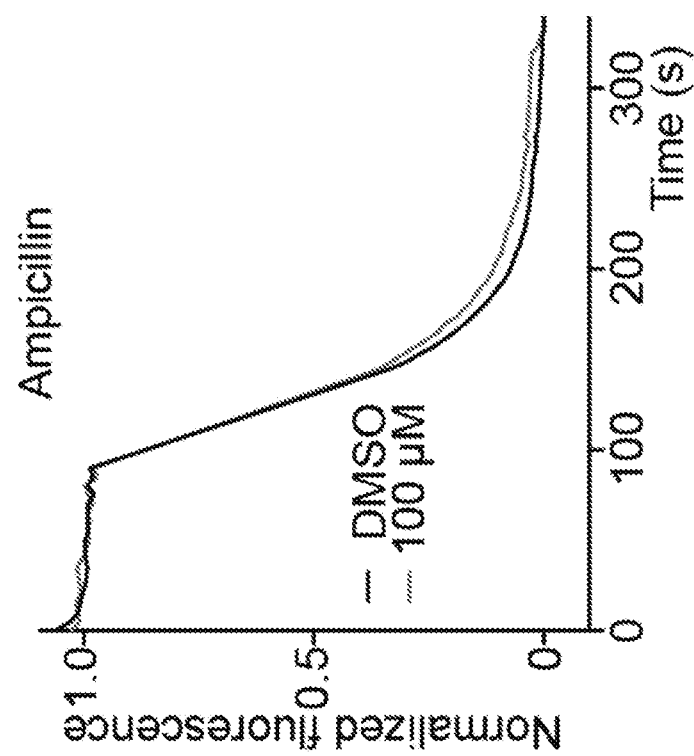
Figure 4G:
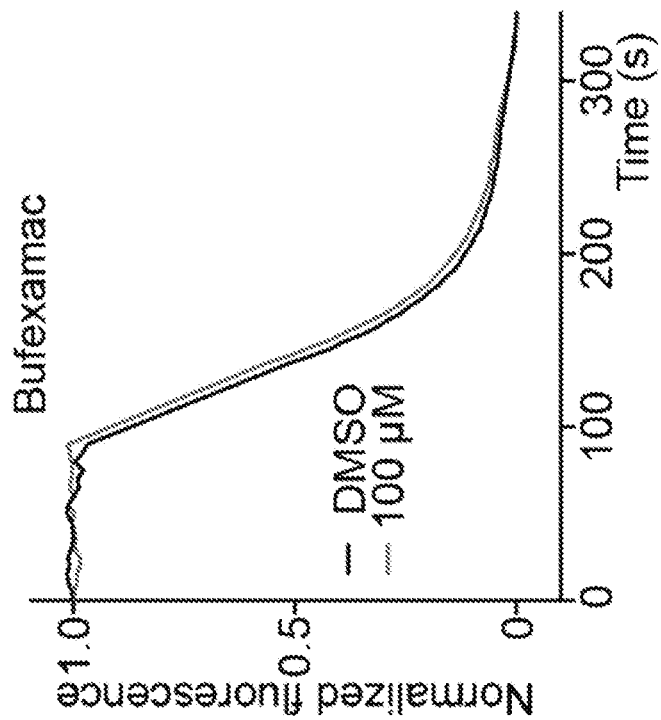
Figure 4H:
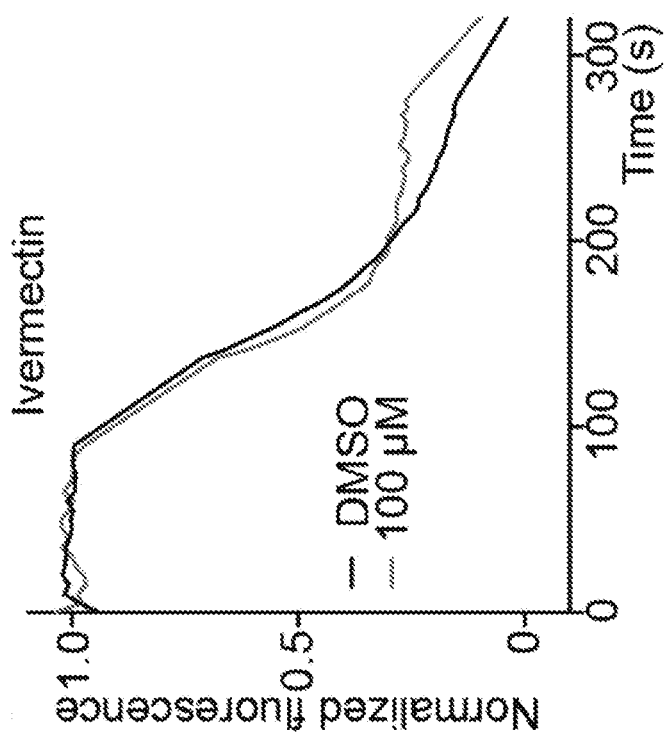
Figure 4I:
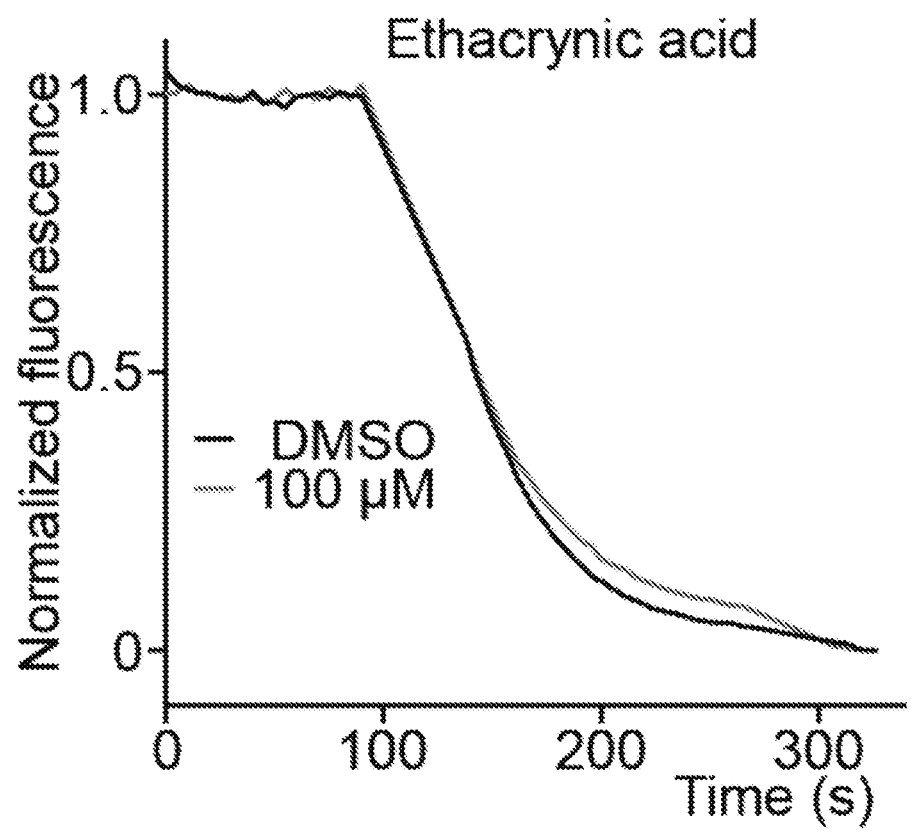
Figure 5:
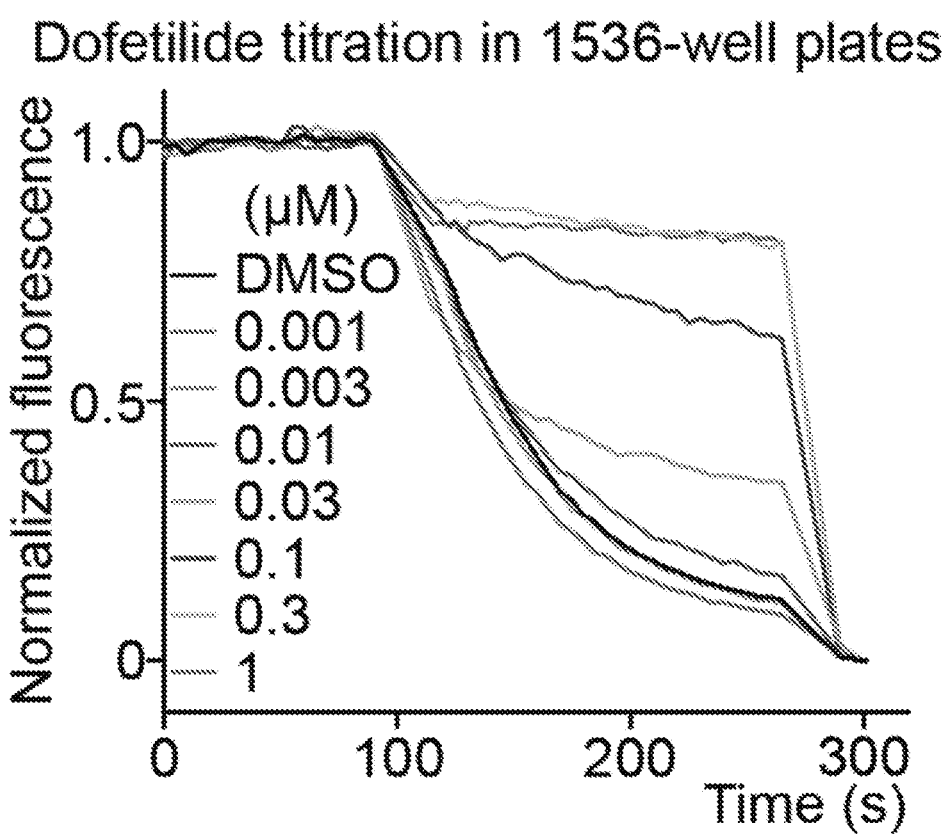
FIG. 5. hERG-mediated efflux in 1536-well plates. Dofetilide was used as a test positive drug. The flux reaction volume was reduced to a quarter of that used in a 384-well plate maintaining all component ratios. The kinetics and inhibitory activity of dofetilide in the 1536-well plate was similar to values using the 384 wells.

If a blocker at concentration x inhibits $K^+$ Conductance according to $$G_K = G_{K0} \times \left(1 - \frac{x}{K_d + x}\right), \quad (2)$$

where $G_{K0}$ is the $K^+$ Conductance in the absence of blocker, then $$G_{tot} = (G_K^{-1} + G_H^{-1})^{-1} = \left(\left(G_{K0} \times \left(1 - \frac{x}{K_d + x}\right)\right)^{-1} + G_H^{-1}\right)^{-1}, \quad (3)$$

where $K_d$ is the equilibrium dissociation constant for the blocker binding to its inhibitory site on the channel FIG. 2G shows that a titration curve is shifted approximately 10-fold when $G_{K0} = 10\ G_H$. By setting $$G_{tot} = (G_{K0}^{-1} + G_H^{-1})^{-1}/2 \quad (4)$$

We find that the IC50 for the LFA curve is $$IC50 = \left(\frac{G_{K0}}{G_H} + 1\right) \times K_d. \quad (5)$$

This model explains in simple terms why LFA can contain an offset in the estimated affinity of a blocker. As shown by the absence of false negative and false positive determinations in Tables 1 and 2, respectively, the offset does not render the assay inaccurate in its ability to identify channel blocking agents.

Data Analysis

All data are presented as mean±SEM.

Flux titration data were first normalized to eliminate baseline fluorescence fluctuations (due to ACMA pipetting variance and intrinsic fluorescence of testing compounds) using the following equation:

$$F_{normalized} = \frac{F - F_{end}}{F_{start} - F_{end}} \quad (6)$$

where $F_{normalized}$ is the normalized fluorescence plotted in the flux titration figures, F is measured fluorescence in arbitrary units, $F_{start}$ is the average of measured fluorescence before addition of CCCP, and $F_{end}$ is the measured endpoint fluorescence after addition of valinomycin. Normalizations were performed with Excel (Microsoft). Plots were made using Prism software (GraphPad).

The initial slopes of flux after CCCP addition (the average slopes of first 10 s after CCCP addition) were extracted from normalized flux titration data. The slope values were normalized to the maximum slope to obtain normalized flux activity plotted in the dose-response curves of flux titrations. Of note, in an inhibitor titration, the maximum slope is the slope of DMSO control whereas in an activator titration the maximum slope is the slope at highest activator concentration tested. The dose-response curves of flux titrations were fitted with the Hill equation with OriginPro software (OriginLab):

$$y = START + (END - START)\frac{x^n}{k^n + x^n} \quad (7)$$

where y is the normalized flux activity (the normalized initial slope), START is the normalized flux activity of DMSO control, END is the normalized flux activity at the highest drug concentration tested, x is drug concentration, and n is the Hill coefficient. The Hill coefficient ranged between 0.8 and 3.2.

The scatter plot of hERG positive control drugs (FIG. 2F) was fitted with linear regression in OriginPro (OriginLab).

In the specification, numerous specific details are set forth in order to provide a thorough understanding of the present embodiments. It will be apparent, however, to one having ordinary skill in the art that the specific detail need not be employed to practice the present embodiments. In other instances, well-known materials or methods have not been described in detail in order to avoid obscuring the present embodiments.

Throughout this specification, quantities are defined by ranges, and by lower and upper boundaries of ranges. Each lower boundary can be combined with each upper boundary to define a range. The lower and upper boundaries should each be taken as a separate element.

Reference throughout this specification to "one embodiment," "an embodiment," "one example," or "an example" means that a particular feature, structure or characteristic described in connection with the embodiment or example is included in at least one embodiment of the present embodiments. Thus, appearances of the phrases "in one embodiment," "in an embodiment," "one example," or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

As used herein, the terms "comprises," "comprising," "includes," "including," "has," "having," or any other variation thereof, are intended to cover a non-exclusive inclusion. For example, a process, article, or apparatus that comprises a list of elements is not necessarily limited to only those elements but may include other elements not expressly listed or inherent to such process, article, or apparatus.

Further, unless expressly stated to the contrary, "or" refers to an inclusive "or" and not to an exclusive "or". For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of any term or terms with which they are utilized. Instead, these examples or illustrations are to be regarded as being described with respect to one particular embodiment and as being illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such nonlimiting examples and illustrations includes, but is not limited to: "for example," "for instance," "e.g.," and "in one embodiment."

In this specification, groups of various parameters containing multiple members are described. Within a group of parameters, each member may be combined with any one or more of the other members to make additional sub-groups. For example, if the members of a group are a, b, c, d, and e, additional sub-groups specifically contemplated include any one, two, three, or four of the members, e.g., a and c; a, d, and e; b, c, d, and e; etc.

TABLE 1

| hERG positive controls | Target | IC50 patch (µM) | IC50 flux (µM) |
|---|---|---|---|
| Amiodarone | class III antiarrhythmic | 0.015-1.071 | 0.447 ± 0.029 |
| Amitriptyline | tricyclic antidepressant | 1.7-3.0 | 12.531 ± 1.320 |
| Amsacrine | antineoplastic | 0.209-0.230 | 1.208 ± 0.036 |
| Aprindine | Class 1b antiarrhythmic | 0.23 | 1.881 ± 0.221 |
| Astemizole | antihistamine | 0.001-0.018 | 0.074 ± 0.005 |
| Azimilide | class III antiarrhythmic | 0.891 | 4.275 ± 1.027 |
| Bepridil | calcium channel blocker | 0.023-0.099 | 0.595 ± 0.066 |
| Chlorpromazine | dopamine antagonist | 0.37 | 3.179 ± 0.297 |
| Cisapride | gastroprokinetic agent | 0.007-0.091 | 0.237 ± 0.014 |
| Clemastine | antihistamine | 0.012 | 0.323 ± 0.018 |
| Clomiphene | estrogen receptor modulator | 0.18 | 4.582 ± 0.598 |
| Cloperastine | cough suppressant | 0.027 | 0.796 ± 0.119 |
| Clotrimazole | antifungal | 1.13 | 12.774 ± 0.304 |
| Cyamemazine | antipsychotic | 0.468 | 7.451 ± 0.308 |
| Dofetilide | class III antiarrhythmic | 0.003-0.015 | 0.038 ± 0.002 |
| Domperidone | anti-dopamine | 0.162 | 0.635 ± 0.069 |
| Doxazosin | alpha blocker | 0.6 | 5.128 ± 0.797 |
| Droperidol | antidopaminergic | 0.100-0.307 | 0.806 ± 0.064 |
| E-4031 | class III antiarrhythmic | 0.008-0.134 | 0.047 ± 0.003 |
| Eliprodil | NMDA antagonist | 0.02 | 0.110 ± 0.009 |
| Escitalopram | serotonin reuptake inhibitor | 2.6 | 11.005 ± 0.959 |
| Fluoxetine | antidepressant | 0.500-0.720 | 4.179 ± 0.237 |
| Fluspirilene | antipsychotic | 0.003 | 0.164 ± 0.010 |
| GBR-12909 | Dopamine reuptake | 0.007 | 0.233 ± 0.022 |
| Halofantrine | antimalaria | 0.022-0.197 | 0.376 ± 0.018 |
| Haloperidol | antipsychotic | 0.015-0.063 | 0.178 ± 0.014 |
| Ibutilide | class III antiarrhythmic | 0.02 | 0.035 ± 0.002 |
| Ifenprodil | NMDA antagonist | 0.41 | 1.589 ± 0.071 |
| Imipramine | tricyclic antidepressant | 1.9 | 14.934 ± 1.618 |
| KB-R7943 | Na/Ca exchanger inhibitor | 0.089 | 1.775 ± 0.140 |
| Ketanserin | antihypertensive | 0.121-0.128 | 1.590 ± 0.247 |
| Ketoconazole | Antifungal | 1.9 | 19.653 ± 2.394 |
| Lidoflazine | calcium channel blocker | 0.017-0.037 | 0.225 ± 0.021 |
| Maprotiline | tetracyclic antidepressants | 3.1-5.2 | 4.882 ± 0.314 |
| Mefloquine | antimalaria | 2.6-5.6 | 2.969 ± 0.421 |
| Mesoridazine | piperidine neuroleptic | 0.426 | 6.647 ± 1.393 |
| Mibefradil | Ca channel blocker | 1.4 | 2.650 ± 0.141 |
| Pimozide | antipsychotic | 0.001-0.018 | 0.081 ± 0.014 |
| Quinidine | class I antiarrhythmic | 0.320-1.5 | 5.520 ± 1.254 |
| Risperidone | antipsychotic | 0.282 | 4.317 ± 0.447 |
| Sertindole | antipsychotic | 0.003-0.210 | 0.387 ± 0.015 |
| Tamoxifen | estrogen receptor | 0.777 | 11.874 ± 0.678 |
| Terfenadine | antihistamine | 0.007-0.204 | 0.927 ± 0.036 |
| Terodiline | antispasmodic | 0.375-0.700 | 9.640 ± 1.592 |
| Thioridazine | antipsychotic | 0.116-1.3 | 2.311 ± 0.160 |
| Tolterodine | antimuscarinic | 0.017 | 0.166 ± 0.008 |
| Trazadone | antidepressant | 0.690-2.9 | 9.248 ± 0.529 |
| Trifluoperazine | antipsychotic | 0.234 | 0.734 ± 0.078 |
| Verapamil | calcium channel blocker | 0.143-2.6 | 4.250 ± 0.753 |
| Ziprasidone | antipsychotic | 0.120-0.240 | 4.061 ± 0.475 |

Table 1. IC50 values of 50 hERG positive control drugs determined using LFA and compared to electrophysiology-determined values reported in the literature (n = 3 each). Measured IC50 values were plotted against the upper limit of IC50 values in electrophysiology in FIG. 2F. No false negative drugs were found. All data are mean ± SEM.

TABLE 2

| hERG negative controls | Target | Percentage inhibition (%) at 100 μM |
|---|---|---|
| Acetaminophen | pain medication | 11.6 ± 7.5 |
| Acetazolamide | carbonic anhydrase inhibitor | 4.4 ± 1.8 |
| Acrivastine | antihistamine | 16.2 ± 5.7 |
| Amiloride | ENaC channel blocker | 15.4 ± 1.0 |
| Amoxillin | antibiotic | −2.6 ± 9.1 |
| Ampicillin | antibiotic | 5.6 ± 4.7 |
| Arterenol | hormonre and neurotransmitter | 3.7 ± 4.3 |
| Aspirin | pain | −1.6 ± 2.4 |
| Bufexamac | anti-inflammatory | 1.7 ± 6.8 |
| Captopril | ACE inhibitor | 1.8 ± 2.9 |
| Carbachol | acetylcholine receptor agonist | 2.2 ± 4.2 |
| Cetirizine | antihistamine | 11.8 ± 4.3 |
| Cimetidine | antihistamine | 19.9 ± 3.7 |
| Clindamycin | antibiotic | 9.2 ± 4.3 |
| Clonidine | alpha2 agonist | 15.2 ± 5.8 |
| Clozapine N-oxide | DREADD agonist | 2.1 ± 3.0 |
| Doxycycline | antibiotic | 1.6 ± 8.7 |
| Enalapril | ACE inhibitor | −0.3 ± 6.8 |
| Ethacrynic acid | loop diuretics | 8.1 ± 4.4 |
| Famotidine | antihistamine | −11.1 ± 15.8 |
| Furosemide | hypertension and edema | −3.7 ± 16.1 |
| Geldanamycin | antitumor antibiotic | −1.5 ± 2.3 ** (10 μM) |
| Glyburide | antidiabetic | 4.0 ± 12.0 |
| Guaifenesin | expectorant | −3.5 ± 7.4 |
| HMR-1556 | KCNQ1 blocker | 6.5 ± 6.9 |
| Ibuprofen | anti-inflammatory | 13.1 ± 2.1 |
| Indapamide | diuretic | 4.8 ± 6.7 |
| Ivermectin | antiparasitic | −21 ± 2.9 |
| Kynurenic acid | antiexcitotoxic | −8.3 ± 4.8 |
| Lidocaine | NaV blocker | 13.0 ± 2.8 |
| Midodrine | vasopressor | 8.2 ± 4.8 |
| Minocycline | antibiotic | −2.5 ± 11.9 |
| N-acetylprocainamide | Class III antiarrhythmic | 14.6 ± 4.2 |
| Naproxen | Cyclooxygenase inhibitor | 3.8 ± 9.9 |
| Oxypeucedanin | anti-tumor | 4.5 ± 19.3 |
| Penicillin | antibiotic | −0.4 ± 9.5 |
| Pentamidine | antimicrobial | 22.8 ± 1.4 |
| Phenylephrine | α1-adrenergic receptor agonist | 0.7 ± 5.9 |
| Picrotoxin | GABAA channel blocker | 3.3 ± 4.0 |
| Pyridoxine | vitamin B6 | −5.0 ± 3.7 |
| Ranitidine | antihistamine | 14.9 ± 2.9 |
| Resveratrol | natural phenol | 21.1 ± 8.6 |
| Salbutamol | beta2 agonist | −6.6 ± 3.3 |
| Spiramycin | antibiotic | −5.8 ± 10.7 |
| Sulfamethoxazole | antibiotic | 11.5 ± 4.3 |
| Sulindac | anti-inflammatory | 1.1 ± 2.8 |
| Thalidomide | immunomodulatory | 9.5 ± 8.1 |
| Trimethoprim | antibiotic | 20.6 ± 1.9 |
| Warfarin | anticoagulant | 9.1 ± 5.5 |
| Wortmannin | PI3K inhibitor | 1.7 ± 5.8 |

Table 2. Percent blockage of 50 hERG negative drugs determined by LFA. Drugs were tested at a concentration of 100 μM except for Geldanamycin, which was tested at 10 μM due to its auto fluorescence (n = 3 each). No drugs induced more than 25% difference compared with DMSO controls at this high concentration and were all considered negative. No false positives were found. All data are mean ± SEM.

INCORPORATION OF SEQUENCE LISTING

Incorporated herein by reference in its entirety is the Sequence Listing for the application. The Sequence Listing is disclosed on a computer-readable ASCII text file titled, "Sequence_Listing_1119-42_PCT.txt", created on Mar. 30, 2017. The sequence-listing.txt file is 26.6 KB in size.

REFERENCES

1. Yu, F. H., Yarov-Yarovoy, V., Gutman, G. A. & Catterall, W. A. Overview of molecular relationships in the voltage-gated ion channel superfamily. *Pharmacological Reviews* 57,387-395 (2005).
2. Shieh, C.-C., Coghlan, M., Sullivan, J. P. & Gopalakrishnan, M. Potassium Channels: Molecular Defects, Diseases, and Therapeutic Opportunities. *Pharmacological Reviews* 52, 557-594 (2000).
3. Hibino, H. et al. Inwardly rectifying potassium channels: their structure, function, and physiological roles. *Physiological Reviews* 90,291-366 (2010).
4. Brohawn, S. G., del Marmol, J. & MacKinnon, R. Crystal structure of the human K2P TRAAK, a lipid- and mechano-sensitive K+ ion channel. *Science* 335,436-441 (2012).
5. Brohawn, S. G., Su, Z. & MacKinnon, R. Mechanosensitivity is mediated directly by the lipid membrane in TRAAK and TREK1 K+ channels. *Proc. Natl. Acad. Sci. U.S.A.* 111, 3614-3619 (2014).
6. Brohawn, S. G., Campbell, E. B. & MacKinnon, R. Physical mechanism for gating and mechanosensitivity of the human TRAAK K+ channel. *Nature* 516,126-130 (2014).
7. Honoré, E. The neuronal background K2P channels: focus on TREK1. *Nat Rev Neurosci* 8,251-261 (2007).
8. Vandenberg, J. I. et al. hERG K+Channels: Structure, Function, and Clinical Significance. *Physiological Reviews* 92,1393-1478 (2012).
9. Nardi, A. & Olesen, S.-P. BK channel modulators: a comprehensive overview. *Curr. Med. Chem.* 15,1126-1146 (2008).
10. Ponte, C. G. et al. Selective, Direct Activation of High-Conductance, Calcium-Activated Potassium Channels Causes Smooth Muscle Relaxation. *Molecular Pharmacology* 81,567-577 (2012).
11. Semenov, I., Wang, B., Herlihy, J. T. & Brenner, R. BK channel beta1-subunit regulation of calcium handling and constriction in tracheal smooth muscle. *AJP: Lung Cellular and Molecular Physiology* 291, L802-10 (2006).
12. Bentzen, B. H., Olesen, S.-P., Rønn, L. C. B. & Grunnet, M. BK channel activators and their therapeutic perspectives. *Front Physiol* 5,389 (2014).
13. Seibold, M. A. et al. An african-specific functional polymorphism in KCNMB1 shows sex-specific association with asthma severity. *Human Molecular Genetics* 17, 2681-2690 (2008).
14. Petkov, G. V. et al. Beta1-subunit of the Ca2+-activated K+ channel regulates contractile activity of mouse urinary bladder smooth muscle. *The Journal of Physiology* 537, 443-452 (2001).
15. Eichhorn, B. & Dobrev, D. Vascular large conductance calcium-activated potassium channels: functional role and therapeutic potential. *Naunyn-Schmied Arch Pharmacol* 376, 145-155 (2007).
16. Schroeder, K., Neagle, B., Trezise, D. J. & Worley, J. Ionworks HT: a new high-throughput electrophysiology measurement platform. *Journal of Biomolecular Screening* 8, 50-64 (2003).
17. Dunlop, J., Bowlby, M., Peri, R., Vasilyev, D. & Arias, R. High-throughput electrophysiology: an emerging paradigm for ion-channel screening and physiology. *Nat Rev Drug Discov* 7,358-368 (2008).
18. Beacham, D. W., Blackmer, T., O'Grady, M. & Hanson, G. T. Cell-Based Potassium Ion Channel Screening Using the FluxOR™ Assay. *Journal of Biomolecular Screening* 15, 441-446 (2010).
19. Whiteaker, K. L. et al. Validation of FLIPR membrane potential dye for high throughput screening of potassium channel modulators. *Journal of Biomolecular Screening* 6, 305-312 (2001).

20. Priest, B., Bell, I. M. & Garcia, M. Role of hERG potassium channel assays in drug development. *channels* 2,87-93 (2014).
21. Huang, X.-P., Mangano, T., Hufeisen, S., Setola, V. & Roth, B. L. Identification of Human Ether-à-go-goRelated Gene Modulators by Three Screening Platforms in an Academic Drug-Discovery Setting. *ASSAY and Drug Development Technologies* 8,727-742 (2010).
22. Wang, W, MacKinnon, R. Cryo-EM structure of the open human ether-à-go-go related K+ channel hERG (cell in press)
23. Goehring, A. et al. Screening and large-scale expression of membrane proteins in mammalian cells for structural studies. *Nat Protoc* 9,2574-2585 (2014).
24. Rothbauer, U. et al. A versatile nanotrap for biochemical and functional studies with fluorescent fusion proteins. *Mol. Cell Proteomics* 7,282-289 (2008).
25. Fridy, P. C. et al. A robust pipeline for rapid production of versatile nanobody repertoires. *Nat Meth* 11,1253-1260 (2014).

The invention claimed is:

1. An engineered hERG channel protein having deletion of residues of region 1 and region 2 of the wild type sequence of the hERG channel protein and selected from the polypeptide consisting of SEQ ID NO. 3 or a polypeptide having deletion of residues positions 120 to 410 (region 1) and residue positions 850 to 1070 (region 2) of wild type hERG protein and that has at least 90% identity to SEQ ID NO. 3, wherein said polypeptide retains hERG channel protein potassium ion channel function.

2. A vesicle comprising: a liposome and an engineered hERG channel protein of claim 1.

3. The vesicle according to claim 2, wherein the liposome further comprises a lipophilic pH-sensitive dye.

4. The vesicle according to claim 3, wherein the lipophilic pH-sensitive dye is selected from the group consisting of: 9-amino-6-chloro-2-methoxyacridine (ACMA), monoamine and diamine acridine orange (AO).

5. The vesicle according claim 2, wherein the vesicle further comprises a proton ionophore.

6. The vesicle according to claim 5, wherein the proton ionophore comprises carbonyl cyanide m-chlorophenylhydrazone (CCCP).

7. The vesicle according to claim 3, wherein the vesicle further comprises a proton ionophore.

8. The vesicle according to claim 4, wherein the vesicle further comprises a proton ionophore.

9. A method of identifying a small molecule pharmacological agent that interferes with repolarization of cardiac cells, the method comprising:
 (a) contacting the vesicle of claim 2 with:
  (i.) said pharmacological agent, and
  (ii.) a pH-sensitive fluorescent dye;
 (b) measuring fluorescence;
 (c) contacting said vesicle with a proton ionophore to initiate ion flux;
 (d) measuring pH-sensitive fluorescence of the dye; and
 (e) identifying the small molecule pharmacological agent as a small molecule pharmacological agent that inhibits hERG function when the fluorescence level at step (d) has no significant loss of fluorescence and is substantially similar to the fluorescence level at step (b), wherein substantially similar is less than 5% reduction, less than 10% reduction, less than 20% reduction, less than 25% reduction, or less than 35% reduction in fluorescence from the fluorescence level at step (b).

10. The method according to claim 9, wherein the pH-sensitive fluorescent dye comprises: 9-amino-6-chloro-2-methoxyacridine (ACMA).

11. The method according to claim 9, wherein the proton ionophore comprises carbonyl cyanide m-chlorophenylhydrazone (CCCP).

12. The method according to claim 9, wherein the vesicle is contacted with a potassium ionophore after step (d).

13. The method according to claim 12, wherein the potassium ionophore is valinomycin.

14. The method according to claim 12, further including measuring pH-sensitive fluorescence of the dye after addition of a potassium ionophore.

15. The method according to claim 9, wherein steps (a)-(d) are done in a multi-well assay plate.

16. The method according to claim 15, wherein the multi-well assay plate contains at least 96 wells, at least 384 wells, or at least 1536 wells.

17. The method according to claim 13, further including measuring pH-sensitive fluorescence of the dye after addition of a potassium ionophore.

\* \* \* \* \*

SEQUENCE LISTING

```
<160> NUMBER OF SEQ ID NOS: 3

<210> SEQ ID NO 1
<211> LENGTH: 1159
<212> TYPE: PRT
<213> ORGANISM: Artificial Sequence
<220> FEATURE:
<223> OTHER INFORMATION: Synthetic peptide sequence

<400> SEQUENCE: 1

Met Pro Val Arg Arg Gly His Val Ala Pro Gln Asn Thr Phe Leu Asp
1               5                   10                  15

Thr Ile Ile Arg Lys Phe Glu Gly Gln Ser Arg Lys Phe Ile Ile Ala
            20                  25                  30

Asn Ala Arg Val Glu Asn Cys Ala Val Ile Tyr Cys Asn Asp Gly Phe
        35                  40                  45

Cys Glu Leu Cys Gly Tyr Ser Arg Ala Glu Val Met Gln Arg Pro Cys
    50                  55                  60

Thr Cys Asp Phe Leu His Gly Pro Arg Thr Gln Arg Arg Ala Ala Ala
65                  70                  75                  80

Gln Ile Ala Gln Ala Leu Leu Gly Ala Glu Glu Arg Lys Val Glu Ile
                85                  90                  95

Ala Phe Tyr Arg Lys Asp Gly Ser Cys Phe Leu Cys Leu Val Asp Val
            100                 105                 110

Val Pro Val Lys Asn Glu Asp Gly Ala Val Ile Met Phe Ile Leu Asn
        115                 120                 125

Phe Glu Val Val Met Glu Lys Asp Met Val Gly Ser Pro Ala His Asp
    130                 135                 140

Thr Asn His Arg Gly Pro Pro Thr Ser Trp Leu Ala Pro Gly Arg Ala
145                 150                 155                 160

Lys Thr Phe Arg Leu Lys Leu Pro Ala Leu Leu Ala Leu Thr Ala Arg
                165                 170                 175

Glu Ser Ser Val Arg Ser Gly Gly Ala Gly Gly Ala Gly Ala Pro Gly
            180                 185                 190

Ala Val Val Val Asp Val Asp Leu Thr Pro Ala Ala Pro Ser Ser Glu
        195                 200                 205

Ser Leu Ala Leu Asp Glu Val Thr Ala Met Asp Asn His Val Ala Gly
    210                 215                 220

Leu Gly Pro Ala Glu Glu Arg Arg Ala Leu Val Gly Pro Gly Ser Pro
225                 230                 235                 240

Pro Arg Ser Ala Pro Gly Gln Leu Pro Ser Pro Arg Ala His Ser Leu
                245                 250                 255

Asn Pro Asp Ala Ser Gly Ser Ser Cys Ser Leu Ala Arg Thr Arg Ser
            260                 265                 270

Arg Glu Ser Cys Ala Ser Val Arg Arg Ala Ser Ser Ala Asp Asp Ile
        275                 280                 285
```

-continued

```
Glu Ala Met Arg Ala Gly Val Leu Pro Pro Pro Arg His Ala Ser
            290                 295                 300
Thr Gly Ala Met His Pro Leu Arg Ser Gly Leu Leu Asn Ser Thr Ser
305                 310                 315                 320
Asp Ser Asp Leu Val Arg Tyr Arg Thr Ile Ser Lys Ile Pro Gln Ile
                325                 330                 335
Thr Leu Asn Phe Val Asp Leu Lys Gly Asp Pro Phe Leu Ala Ser Pro
            340                 345                 350
Thr Ser Asp Arg Glu Ile Ile Ala Pro Lys Ile Lys Glu Arg Thr His
            355                 360                 365
Asn Val Thr Glu Lys Val Thr Gln Val Leu Ser Leu Gly Ala Asp Val
370                 375                 380
Leu Pro Glu Tyr Lys Leu Gln Ala Pro Arg Ile His Arg Trp Thr Ile
385                 390                 395                 400
Leu His Tyr Ser Pro Phe Lys Ala Val Trp Asp Trp Leu Ile Leu Leu
                405                 410                 415
Leu Val Ile Tyr Thr Ala Val Phe Thr Pro Tyr Ser Ala Ala Phe Leu
                420                 425                 430
Leu Lys Glu Thr Glu Glu Gly Pro Pro Ala Thr Glu Cys Gly Tyr Ala
            435                 440                 445
Cys Gln Pro Leu Ala Val Val Asp Leu Ile Val Asp Ile Met Phe Ile
450                 455                 460
Val Asp Ile Leu Ile Asn Phe Arg Thr Thr Tyr Val Asn Ala Asn Glu
465                 470                 475                 480
Glu Val Val Ser His Pro Gly Arg Ile Ala Val His Tyr Phe Lys Gly
                485                 490                 495
Trp Phe Leu Ile Asp Met Val Ala Ala Ile Pro Phe Asp Leu Leu Ile
            500                 505                 510
Phe Gly Ser Gly Ser Glu Glu Leu Ile Gly Leu Leu Lys Thr Ala Arg
            515                 520                 525
Leu Leu Arg Leu Val Arg Val Ala Arg Lys Leu Asp Arg Tyr Ser Glu
530                 535                 540
Tyr Gly Ala Ala Val Leu Phe Leu Leu Met Cys Thr Phe Ala Leu Ile
545                 550                 555                 560
Ala His Trp Leu Ala Cys Ile Trp Tyr Ala Ile Gly Asn Met Glu Gln
                565                 570                 575
Pro His Met Asp Ser Arg Ile Gly Trp Leu His Asn Leu Gly Asp Gln
            580                 585                 590
Ile Gly Lys Pro Tyr Asn Ser Ser Gly Leu Gly Gly Pro Ser Ile Lys
            595                 600                 605
Asp Lys Tyr Val Thr Ala Leu Tyr Phe Thr Phe Ser Ser Leu Thr Ser
            610                 615                 620
Val Gly Phe Gly Asn Val Ser Pro Asn Thr Asn Ser Glu Lys Ile Phe
625                 630                 635                 640
Ser Ile Cys Val Met Leu Ile Gly Ser Leu Met Tyr Ala Ser Ile Phe
                645                 650                 655
Gly Asn Val Ser Ala Ile Ile Gln Arg Leu Tyr Ser Gly Thr Ala Arg
            660                 665                 670
Tyr His Thr Gln Met Leu Arg Val Arg Glu Phe Ile Arg Phe His Gln
            675                 680                 685
Ile Pro Asn Pro Leu Arg Gln Arg Leu Glu Glu Tyr Phe Gln His Ala
            690                 695                 700
```

```
Trp Ser Tyr Thr Asn Gly Ile Asp Met Asn Ala Val Leu Lys Gly Phe
705                 710                 715                 720

Pro Glu Cys Leu Gln Ala Asp Ile Cys Leu His Leu Asn Arg Ser Leu
            725                 730                 735

Leu Gln His Cys Lys Pro Phe Arg Gly Ala Thr Lys Gly Cys Leu Arg
        740                 745                 750

Ala Leu Ala Met Lys Phe Lys Thr Thr His Ala Pro Pro Gly Asp Thr
    755                 760                 765

Leu Val His Ala Gly Asp Leu Leu Thr Ala Leu Tyr Phe Ile Ser Arg
770                 775                 780

Gly Ser Ile Glu Ile Leu Arg Gly Asp Val Val Ala Ile Leu Gly
785                 790                 795                 800

Lys Asn Asp Ile Phe Gly Glu Pro Leu Asn Leu Tyr Ala Arg Pro Gly
                805                 810                 815

Lys Ser Asn Gly Asp Val Arg Ala Leu Thr Tyr Cys Asp Leu His Lys
            820                 825                 830

Ile His Arg Asp Asp Leu Leu Glu Val Leu Asp Met Tyr Pro Glu Phe
        835                 840                 845

Ser Asp His Phe Trp Ser Ser Leu Glu Ile Thr Phe Asn Leu Arg Asp
850                 855                 860

Thr Asn Met Ile Pro Gly Ser Pro Gly Ser Thr Glu Leu Glu Gly Gly
865                 870                 875                 880

Phe Ser Arg Gln Arg Lys Arg Lys Leu Ser Phe Arg Arg Thr Asp
                885                 890                 895

Lys Asp Thr Glu Gln Pro Gly Glu Val Ser Ala Leu Gly Pro Gly Arg
            900                 905                 910

Ala Gly Ala Gly Pro Ser Ser Arg Gly Arg Pro Gly Gly Pro Trp Gly
        915                 920                 925

Glu Ser Pro Ser Ser Gly Pro Ser Pro Glu Ser Ser Glu Asp Glu
930                 935                 940

Gly Pro Gly Arg Ser Ser Ser Pro Leu Arg Leu Val Pro Phe Ser Ser
945                 950                 955                 960

Pro Arg Pro Pro Gly Glu Pro Gly Gly Glu Pro Leu Met Glu Asp
                965                 970                 975

Cys Glu Lys Ser Ser Asp Thr Cys Asn Pro Leu Ser Gly Ala Phe Ser
            980                 985                 990

Gly Val Ser Asn Ile Phe Ser Phe Trp Gly Asp Ser Arg Gly Arg Gln
        995                 1000                1005

Tyr Gln Glu Leu Pro Arg Cys Pro Ala Pro Thr Pro Ser Leu Leu
    1010                1015                1020

Asn Ile Pro Leu Ser Ser Pro Gly Arg Arg Pro Arg Gly Asp Val
    1025                1030                1035

Glu Ser Arg Leu Asp Ala Leu Gln Arg Gln Leu Asn Arg Leu Glu
    1040                1045                1050

Thr Arg Leu Ser Ala Asp Met Ala Thr Val Leu Gln Leu Leu Gln
    1055                1060                1065

Arg Gln Met Thr Leu Val Pro Ala Tyr Ser Ala Val Thr Thr
    1070                1075                1080

Pro Gly Pro Gly Pro Thr Ser Thr Ser Pro Leu Leu Pro Val Ser
    1085                1090                1095

Pro Leu Pro Thr Leu Thr Leu Asp Ser Leu Ser Gln Val Ser Gln
    1100                1105                1110

Phe Met Ala Cys Glu Glu Leu Pro Pro Gly Ala Pro Glu Leu Pro
```

```
                1115                1120                1125

Gln Glu  Gly Pro Thr Arg Arg  Leu Ser Leu Pro Gly  Gln Leu Gly
         1130                 1135                 1140

Ala Leu  Thr Ser Gln Pro Leu  His Arg His Gly Ser  Asp Pro Gly
         1145                 1150                 1155

Ser

<210> SEQ ID NO 2
<211> LENGTH: 1159
<212> TYPE: PRT
<213> ORGANISM: Artificial Sequence
<220> FEATURE:
<223> OTHER INFORMATION: Synthetic peptide sequence

<400> SEQUENCE: 2

Met Ala Val Arg Arg Gly His Val Ala Pro Gln Asn Thr Phe Leu Asp
1               5                   10                  15

Thr Ile Ile Arg Lys Phe Glu Gly Gln Ser Arg Lys Phe Ile Ile Ala
                20                  25                  30

Asn Ala Arg Val Glu Asn Cys Ala Val Ile Tyr Cys Asn Asp Gly Phe
            35                  40                  45

Cys Glu Leu Cys Gly Tyr Ser Arg Ala Glu Val Met Gln Arg Pro Cys
    50                  55                  60

Thr Cys Asp Phe Leu His Gly Pro Arg Thr Gln Arg Arg Ala Ala Ala
65                  70                  75                  80

Gln Ile Ala Gln Ala Leu Leu Gly Ala Glu Glu Arg Lys Val Glu Ile
                85                  90                  95

Ala Phe Tyr Arg Lys Asp Gly Ser Cys Phe Leu Cys Leu Val Asp Val
            100                 105                 110

Val Pro Val Lys Asn Glu Asp Gly Ala Val Ile Met Phe Ile Leu Asn
        115                 120                 125

Phe Glu Val Val Met Glu Lys Asp Met Val Gly Ser Pro Ala His Asp
130                 135                 140

Thr Asn His Arg Gly Pro Pro Thr Ser Trp Leu Ala Pro Gly Arg Ala
145                 150                 155                 160

Lys Thr Phe Arg Leu Lys Leu Pro Ala Leu Leu Ala Leu Thr Ala Arg
                165                 170                 175

Glu Ser Ser Val Arg Ser Gly Gly Ala Gly Gly Ala Gly Ala Pro Gly
            180                 185                 190

Ala Val Val Val Asp Val Asp Leu Thr Pro Ala Ala Pro Ser Ser Glu
        195                 200                 205

Ser Leu Ala Leu Asp Glu Val Thr Ala Met Asp Asn His Val Ala Gly
    210                 215                 220

Leu Gly Pro Ala Glu Glu Arg Arg Ala Leu Val Gly Pro Gly Ser Pro
225                 230                 235                 240

Pro Arg Ser Ala Pro Gly Gln Leu Pro Ser Pro Arg Ala His Ser Leu
                245                 250                 255

Asn Pro Asp Ala Ser Gly Ser Ser Cys Ser Leu Ala Arg Thr Arg Ser
            260                 265                 270

Arg Glu Ser Cys Ala Ser Val Arg Ala Ser Ser Ala Asp Asp Ile
        275                 280                 285

Glu Ala Met Arg Ala Gly Val Leu Pro Pro Pro Arg His Ala Ser
    290                 295                 300

Thr Gly Ala Met His Pro Leu Arg Ser Gly Leu Leu Asn Ser Thr Ser
305                 310                 315                 320
```

```
Asp Ser Asp Leu Val Arg Tyr Arg Thr Ile Ser Lys Ile Pro Gln Ile
            325                 330                 335

Thr Leu Asn Phe Val Asp Leu Lys Gly Asp Pro Phe Leu Ala Ser Pro
            340                 345                 350

Thr Ser Asp Arg Glu Ile Ile Ala Pro Lys Ile Lys Glu Arg Thr His
            355                 360                 365

Asn Val Thr Glu Lys Val Thr Gln Val Leu Ser Leu Gly Ala Asp Val
            370                 375                 380

Leu Pro Glu Tyr Lys Leu Gln Ala Pro Arg Ile His Arg Trp Thr Ile
385                 390                 395                 400

Leu His Tyr Ser Pro Phe Lys Ala Val Trp Asp Trp Leu Ile Leu Leu
            405                 410                 415

Leu Val Ile Tyr Thr Ala Val Phe Thr Pro Tyr Ser Ala Ala Phe Leu
            420                 425                 430

Leu Lys Glu Thr Glu Glu Gly Pro Pro Ala Thr Glu Cys Gly Tyr Ala
            435                 440                 445

Cys Gln Pro Leu Ala Val Val Asp Leu Ile Val Asp Ile Met Phe Ile
            450                 455                 460

Val Asp Ile Leu Ile Asn Phe Arg Thr Thr Tyr Val Asn Ala Asn Glu
465                 470                 475                 480

Glu Val Val Ser His Pro Gly Arg Ile Ala Val His Tyr Phe Lys Gly
            485                 490                 495

Trp Phe Leu Ile Asp Met Val Ala Ala Ile Pro Phe Asp Leu Leu Ile
            500                 505                 510

Phe Gly Ser Gly Ser Glu Glu Leu Ile Gly Leu Leu Lys Thr Ala Arg
            515                 520                 525

Leu Leu Arg Leu Val Arg Val Ala Arg Lys Leu Asp Arg Tyr Ser Glu
            530                 535                 540

Tyr Gly Ala Ala Val Leu Phe Leu Leu Met Cys Thr Phe Ala Leu Ile
545                 550                 555                 560

Ala His Trp Leu Ala Cys Ile Trp Tyr Ala Ile Gly Asn Met Glu Gln
            565                 570                 575

Pro His Met Asp Ser Arg Ile Gly Trp Leu His Asn Leu Gly Asp Gln
            580                 585                 590

Ile Gly Lys Pro Tyr Asn Ser Ser Gly Leu Gly Gly Pro Ser Ile Lys
            595                 600                 605

Asp Lys Tyr Val Thr Ala Leu Tyr Phe Thr Phe Ser Ser Leu Thr Ser
            610                 615                 620

Val Gly Phe Gly Asn Val Ser Pro Asn Thr Asn Ser Glu Lys Ile Phe
625                 630                 635                 640

Ser Ile Cys Val Met Leu Ile Gly Ser Leu Met Tyr Ala Ser Ile Phe
            645                 650                 655

Gly Asn Val Ser Ala Ile Ile Gln Arg Leu Tyr Ser Gly Thr Ala Arg
            660                 665                 670

Tyr His Thr Gln Met Leu Arg Val Arg Glu Phe Ile Arg Phe His Gln
            675                 680                 685

Ile Pro Asn Pro Leu Arg Gln Arg Leu Glu Glu Tyr Phe Gln His Ala
            690                 695                 700

Trp Ser Tyr Thr Asn Gly Ile Asp Met Asn Ala Val Leu Lys Gly Phe
705                 710                 715                 720

Pro Glu Cys Leu Gln Ala Asp Ile Cys Leu His Leu Asn Arg Ser Leu
            725                 730                 735
```

-continued

Leu Gln His Cys Lys Pro Phe Arg Gly Ala Thr Lys Gly Cys Leu Arg
            740                 745                 750

Ala Leu Ala Met Lys Phe Lys Thr Thr His Ala Pro Pro Gly Asp Thr
            755                 760                 765

Leu Val His Ala Gly Asp Leu Leu Thr Ala Leu Tyr Phe Ile Ser Arg
            770                 775                 780

Gly Ser Ile Glu Ile Leu Arg Gly Asp Val Val Ala Ile Leu Gly
785                 790                 795                 800

Lys Asn Asp Ile Phe Gly Glu Pro Leu Asn Leu Tyr Ala Arg Pro Gly
            805                 810                 815

Lys Ser Asn Gly Asp Val Arg Ala Leu Thr Tyr Cys Asp Leu His Lys
            820                 825                 830

Ile His Arg Asp Asp Leu Leu Glu Val Leu Asp Met Tyr Pro Glu Phe
            835                 840                 845

Ser Asp His Phe Trp Ser Ser Leu Glu Ile Thr Phe Asn Leu Arg Asp
            850                 855                 860

Thr Asn Met Ile Pro Gly Ser Pro Gly Ser Thr Glu Leu Glu Gly Gly
865                 870                 875                 880

Phe Ser Arg Gln Arg Lys Arg Lys Leu Ser Phe Arg Arg Thr Asp
            885                 890                 895

Lys Asp Thr Glu Gln Pro Gly Glu Val Ser Ala Leu Gly Pro Gly Arg
            900                 905                 910

Ala Gly Ala Gly Pro Ser Ser Arg Gly Arg Pro Gly Gly Pro Trp Gly
            915                 920                 925

Glu Ser Pro Ser Ser Gly Pro Ser Ser Pro Gly Ser Ser Glu Asp Glu
            930                 935                 940

Gly Pro Gly Arg Ser Ser Ser Pro Leu Arg Leu Val Pro Phe Ser Ser
945                 950                 955                 960

Pro Arg Pro Pro Gly Glu Pro Pro Gly Gly Glu Pro Leu Met Glu Asp
            965                 970                 975

Cys Glu Lys Ser Ser Asp Thr Cys Asn Pro Leu Ser Gly Ala Phe Ser
            980                 985                 990

Gly Val Ser Asn Ile Phe Ser Phe Trp Gly Asp Ser Arg Gly Arg Gln
            995                 1000                1005

Tyr Gln Glu Leu Pro Arg Cys Pro Ala Pro Thr Pro Ser Leu Leu
            1010                1015                1020

Asn Ile Pro Leu Ser Ser Pro Gly Arg Arg Pro Arg Gly Asp Val
            1025                1030                1035

Glu Ser Arg Leu Asp Ala Leu Gln Arg Gln Leu Asn Arg Leu Glu
            1040                1045                1050

Thr Arg Leu Ser Ala Asp Met Ala Thr Val Leu Gln Leu Leu Gln
            1055                1060                1065

Arg Gln Met Thr Leu Val Pro Pro Ala Tyr Ser Ala Val Thr Thr
            1070                1075                1080

Pro Gly Pro Gly Pro Thr Ser Thr Ser Pro Leu Leu Pro Val Ser
            1085                1090                1095

Pro Leu Pro Thr Leu Thr Leu Asp Ser Leu Ser Gln Val Ser Gln
            1100                1105                1110

Phe Met Ala Cys Glu Glu Leu Pro Pro Gly Ala Pro Glu Leu Pro
            1115                1120                1125

Gln Glu Gly Pro Thr Arg Arg Leu Ser Leu Pro Gly Gln Leu Gly
            1130                1135                1140

Ala Leu Thr Ser Gln Pro Leu His Arg His Gly Ser Asp Pro Gly

Ser

<210> SEQ ID NO 3
<211> LENGTH: 784
<212> TYPE: PRT
<213> ORGANISM: Artificial Sequence
<220> FEATURE:
<223> OTHER INFORMATION: Synthetic peptide sequence

<400> SEQUENCE: 3

```
Met Ala Val Arg Arg Gly His Val Ala Pro Gln Asn Thr Phe Leu Asp
1               5                   10                  15

Thr Ile Ile Arg Lys Phe Glu Gly Gln Ser Arg Lys Phe Ile Ile Ala
                20                  25                  30

Asn Ala Arg Val Glu Asn Cys Ala Val Ile Tyr Cys Asn Asp Gly Phe
            35                  40                  45

Cys Glu Leu Cys Gly Tyr Ser Arg Ala Glu Val Met Gln Arg Pro Cys
        50                  55                  60

Thr Cys Asp Phe Leu His Gly Pro Arg Thr Gln Arg Arg Ala Ala Ala
65                  70                  75                  80

Gln Ile Ala Gln Ala Leu Leu Gly Ala Glu Arg Lys Val Glu Ile
                85                  90                  95

Ala Phe Tyr Arg Lys Asp Gly Ser Cys Phe Leu Cys Leu Val Asp Val
                100                 105                 110

Val Pro Val Lys Asn Glu Asp Gly Ala Val Ile Met Phe Ile Leu Asn
            115                 120                 125

Phe Glu Val Val Met Glu Lys Asp Met Val Gly Ser Gly Ala Asp Val
        130                 135                 140

Leu Pro Glu Tyr Lys Leu Gln Ala Pro Arg Ile His Arg Trp Thr Ile
145                 150                 155                 160

Leu His Tyr Ser Pro Phe Lys Ala Val Trp Asp Trp Leu Ile Leu Leu
                165                 170                 175

Leu Val Ile Tyr Thr Ala Val Phe Thr Pro Tyr Ser Ala Ala Phe Leu
                180                 185                 190

Leu Lys Glu Thr Glu Glu Gly Pro Pro Ala Thr Glu Cys Gly Tyr Ala
            195                 200                 205

Cys Gln Pro Leu Ala Val Val Asp Leu Ile Val Asp Ile Met Phe Ile
        210                 215                 220

Val Asp Ile Leu Ile Asn Phe Arg Thr Thr Tyr Val Asn Ala Asn Glu
225                 230                 235                 240

Glu Val Val Ser His Pro Gly Arg Ile Ala Val His Tyr Phe Lys Gly
                245                 250                 255

Trp Phe Leu Ile Asp Met Val Ala Ala Ile Pro Phe Asp Leu Leu Ile
                260                 265                 270

Phe Gly Ser Gly Ser Glu Glu Leu Ile Gly Leu Leu Lys Thr Ala Arg
            275                 280                 285

Leu Leu Arg Leu Val Arg Val Ala Arg Lys Leu Asp Arg Tyr Ser Glu
        290                 295                 300

Tyr Gly Ala Ala Val Leu Phe Leu Leu Met Cys Thr Phe Ala Leu Ile
305                 310                 315                 320

Ala His Trp Leu Ala Cys Ile Trp Tyr Ala Ile Gly Asn Met Glu Gln
                325                 330                 335

Pro His Met Asp Ser Arg Ile Gly Trp Leu His Asn Leu Gly Asp Gln
                340                 345                 350
```

```
Ile Gly Lys Pro Tyr Asn Ser Ser Gly Leu Gly Gly Pro Ser Ile Lys
        355                 360                 365

Asp Lys Tyr Val Thr Ala Leu Tyr Phe Thr Phe Ser Ser Leu Thr Ser
        370                 375                 380

Val Gly Phe Gly Asn Val Ser Pro Asn Thr Asn Ser Glu Lys Ile Phe
385                 390                 395                 400

Ser Ile Cys Val Met Leu Ile Gly Ser Leu Met Tyr Ala Ser Ile Phe
                405                 410                 415

Gly Asn Val Ser Ala Ile Ile Gln Arg Leu Tyr Ser Gly Thr Ala Arg
                420                 425                 430

Tyr His Thr Gln Met Leu Arg Val Arg Glu Phe Ile Arg Phe His Gln
                435                 440                 445

Ile Pro Asn Pro Leu Arg Gln Arg Leu Glu Glu Tyr Phe Gln His Ala
        450                 455                 460

Trp Ser Tyr Thr Asn Gly Ile Asp Met Asn Ala Val Leu Lys Gly Phe
465                 470                 475                 480

Pro Glu Cys Leu Gln Ala Asp Ile Cys Leu His Leu Asn Arg Ser Leu
                485                 490                 495

Leu Gln His Cys Lys Pro Phe Arg Gly Ala Thr Lys Gly Cys Leu Arg
                500                 505                 510

Ala Leu Ala Met Lys Phe Lys Thr Thr His Ala Pro Pro Gly Asp Thr
        515                 520                 525

Leu Val His Ala Gly Asp Leu Leu Thr Ala Leu Tyr Phe Ile Ser Arg
        530                 535                 540

Gly Ser Ile Glu Ile Leu Arg Gly Asp Val Val Ala Ile Leu Gly
545                 550                 555                 560

Lys Asn Asp Ile Phe Gly Glu Pro Leu Asn Leu Tyr Ala Arg Pro Gly
                565                 570                 575

Lys Ser Asn Gly Asp Val Arg Ala Leu Thr Tyr Cys Asp Leu His Lys
                580                 585                 590

Ile His Arg Asp Asp Leu Leu Glu Val Leu Asp Met Tyr Pro Glu Phe
        595                 600                 605

Ser Asp His Phe Trp Ser Ser Leu Glu Ile Thr Phe Asn Leu Arg Asp
        610                 615                 620

Thr Asn Met Ile Pro Gly Gly Arg Gln Tyr Gln Glu Leu Pro Arg Cys
625                 630                 635                 640

Pro Ala Pro Thr Pro Ser Leu Leu Asn Ile Pro Leu Ser Ser Pro Gly
                645                 650                 655

Arg Arg Pro Arg Gly Asp Val Glu Ser Arg Leu Asp Ala Leu Gln Arg
                660                 665                 670

Gln Leu Asn Arg Leu Glu Thr Arg Leu Ser Ala Asp Met Ala Thr Val
        675                 680                 685

Leu Gln Leu Leu Gln Arg Gln Met Thr Leu Val Pro Pro Ala Tyr Ser
        690                 695                 700

Ala Val Thr Thr Pro Gly Pro Gly Pro Thr Ser Thr Ser Pro Leu Leu
705                 710                 715                 720

Pro Val Ser Pro Leu Pro Thr Leu Thr Leu Asp Ser Leu Ser Gln Val
                725                 730                 735

Ser Gln Phe Met Ala Cys Glu Glu Leu Pro Pro Gly Ala Pro Glu Leu
                740                 745                 750

Pro Gln Glu Gly Pro Thr Arg Arg Leu Ser Leu Pro Gly Gln Leu Gly
        755                 760                 765
```

```
Ala Leu Thr Ser Gln Pro Leu His Arg His Gly Ser Asp Pro Gly Ser
770                 775                 780
```